US005780036A

United States Patent [19]
Chisari

[11] Patent Number: 5,780,036
[45] Date of Patent: Jul. 14, 1998

[54] PEPTIDES FOR INDUCING CYTOTOXIC T LYMPHOCYTE RESPONSES TO HEPATTIS B VIRUS

[75] Inventor: Francis V. Chisari, Del Mar, Calif.

[73] Assignee: The Scripps Research Institute, La Jolla, Calif.

[21] Appl. No.: 416,950

[22] Filed: Apr. 4, 1995

Related U.S. Application Data

[63] Continuation of Ser. No. 100,870, Aug. 2, 1993, abandoned, which is a continuation-in-part of Ser. No. 935,898, Aug. 26, 1992, which is a continuation-in-part of Ser. No. 749,540, Aug. 26, 1991, abandoned.

[51] Int. Cl.$^6$ .................. A61K 39/29; A61K 39/12; A61K 39/385; C07K 7/06
[52] U.S. Cl. .................. 424/189.1; 424/154.1; 424/185.1; 424/186.1; 424/193.1; 424/196.11; 424/204.1; 424/227.1; 514/2; 514/15; 530/300; 530/327; 530/328; 530/403
[58] Field of Search .................. 514/2, 12; 530/300, 530/403, 327, 328; 536/22.1, 23.1, 23.72; 435/69.1, 240.2, 252.3, 320.1; 424/184.1, 185.1, 186.1, 189.1, 193.1, 196.11, 204.1, 227.1

[56] References Cited

U.S. PATENT DOCUMENTS

| | | | |
|---|---|---|---|
| 4,235,877 | 11/1980 | Fullerton | 424/89 |
| 4,428,941 | 1/1984 | Galibert et al. | 427/177 |
| 4,487,715 | 12/1984 | Nitecki | 260/112 |
| 4,599,230 | 7/1986 | Milich et al. | 424/89 |
| 4,599,231 | 7/1986 | Milich et al. | 424/89 |
| 4,818,527 | 4/1989 | Thornton et al. | 424/88 |
| 4,882,145 | 11/1989 | Thorton et al. | 424/88 |
| 4,935,235 | 6/1990 | Rutter et al. | 424/88 |
| 5,017,558 | 5/1991 | Vyas | 514/14 |
| 5,019,386 | 5/1991 | Machida et al. | 424/89 |
| 5,039,522 | 8/1991 | Neurath | 424/89 |
| 5,100,662 | 3/1992 | Bolcsak et al. | 424/88 |

FOREIGN PATENT DOCUMENTS

| | | |
|---|---|---|
| 013828 | 6/1980 | European Pat. Off. |
| 105481 | 4/1984 | European Pat. Off. |
| 431327 | 6/1991 | European Pat. Off. |
| 469281 | 6/1991 | European Pat. Off. |
| 534615 | 3/1992 | European Pat. Off. |
| 161999 | 8/1985 | Japan . |
| 2034323 | 6/1980 | United Kingdom . |
| 93/03753 | 3/1993 | WIPO . |
| 94/03205 | 2/1994 | WIPO . |
| 94/20127 | 9/1994 | WIPO . |

OTHER PUBLICATIONS

Celis et al., "Recognition of Hepatitis B Surface Antigen by Human Lymphocytes" *J. Immunol.* 140:1808–1815 (Mar. 15, 1988).
Carbone et al. "Induction of Cytotoxic T Lymphocytes by Primary in vitro Stimulation with Peptides", *J. Exp. Med.*, 167:1767–1779 (Jun. 1988).
Moore et al., "Introduction of Soluble Protein into the Class I Pathway of Antigen Processing and Presentation", *Cell* 54:777–785 (Sep. 9, 1988).
Milich et al., "Comparative Immunogenicity of Hepatitis B Virus Core and E Antigens", *J. Immunol.* 141:3617–3624 (Nov. 15, 1988).
Gotch et al., "Recognition of Influenza A Matrix Protein by HLA–A2–Restricted Cytotoxic T Lymphocytes", *J. Exp. Med.* 163:2045–2057 (Dec. 1988).
Milich, "T–and B–cell Recognition of Hepatitis B Viral Antigens", *Immunol. Today* 9:380–386 (1988).
Hayashi et al., "Studies on Peptides CLXVI. Solid–Phase Synthesis and Immunological Properties of Fragment Peptides Related to Human Hepatitis B virus Surface Antigen (HBsAg) and Its Pre–S2 Gene" *Chem. Pharm. Bull.* 36(12):4993–4994 (1988).
Braciale et al., "Class I Major Histocompatibility Complex–restricted Cytolytic T Lymphocytes Recognize a Limited Number of sites on the Influenza Hemagglutinin", *Proc. Natl. Acad. Sci. USA* 86:277–281 (Jan. 1989).
Ishioka et al., "Induction of Class I MHC–restricted, Peptide–specific Cytolytic T Lymphocytes by Peptide Priming in vivo", *J. Immonol.*, 143:1094–1100 (Aug. 15, 1989).
Klavinskis et al., "Molecularly Engineered Vaccine Which Expresses an Immunodominant T–cell Epitope Induces Cytotoxic T Lymphocytes that Confer Protection for Lethal Virus Infection," *J. Virol.*, 63:4311–4316 (Oct. 1989).
Bevan, "Stimulating Killer Cells", *Nature* 342:478–479 (Nov. 30, 1989).
Deres et al., "In Vivo Priming of Virus–Specific Cytotoxic T Lymphocytes with Synthetic Lipopeptide Vaccine", *Nature* 342:561–564 (Nov. 30, 1989).
Tam et al., "Vaccine Engineering: Enhancement of Immunogenicity of Synthetic Peptide Vaccines Related to Hepatitis in Chemically Defined Models Consisting of T–and B–cell Epitopes", *Proc. Natl. Acad. Sci. USA* 86:9084–9088 (Dec. 1989).
Chisari et al., "Hepatitis B Virus Structure and Biology", *Microbial Pathogenesis* 6:311–325 (1989).
Moriyama et al., "Immunobiology and Pathogenesis of Hepatocellular Injury in Hepatitis B Virus Transgenic Mice", *Science* 248:361–364 (Apr. 20, 1990).
Aichele et al., "Antiviral Cytotoxic T Cell Response Induced by in vivo Priming with a Free Synthetic Peptide", *J. Exp. Med.*, 171:1815–1820 (May, 1990).

(List continued on next page.)

*Primary Examiner*—Michael P. Woodward
*Attorney, Agent, or Firm*—Townsend and Townsend and Crew

[57] ABSTRACT

Peptides are used to define epitopes that stimulate HLA-restricted cytotoxic T lymphocyte activity against hepatitis B virus antigens. The peptides are derived from regions of HBV polymerase, and are particularly useful in treating or preventing HBV infection, including methods for stimulating the immune response of chronically infected individuals to respond to HBV antigens.

7 Claims, 18 Drawing Sheets

OTHER PUBLICATIONS

Aggarwal et al., "Oral Salmonella: Malaria Circumsporozoite Recombinants Induce Specific CD8+ Cytotoxic T Cells", *J. Exp. Med.*, 172:1083–1090 (Oct. 1990).

Van Bleek et al., "Isolation of an Endogenously Processed Immunodominant Viral Peptide from the Class IH–2K$^b$ Molecule", *Nature* 348:213–216 (Nov. 15, 1990).

Rotzschke et al., "Isolation and Analysis of Naturally Processed Viral Peptides as Recognized by Cytotoxic T cells", *Nature* 348:252–254 (Nov. 15, 1990).

Golvano et al., "Polarity of Immunogens: Implications for Vaccine Design", *Eur. J. Immunol.* 20:2363–2366 (1990).

Ishioka et al., "Class I MHC–restricted, Peptide–specific Cytotoxic T Lymphocytes Generated by Peptide Priming in vivo", *Vaccines 90*, Cold Spring Harbor Press, pp. 7–11 (1990).

Wakita et al "Gamma–Interferon Production Response to Hepatitis B Core Protein & Synthetic Peptides in Patients with Chronic Hepatitis B Virus Infection", *Digestion* 47:149–155 (1990).

Kast et al., "Protection Against Lethal Sendai Virus Infection by in vivo Priming of Virus–specific Cytotoxic T Lymphocytes with a Free Synthetic Peptide", *Proc. Natl. Acad. Sci. USA* 88:2283–2287 (Mar. 1991).

Schumacher et al., "Peptide Selection by MHC Class I Molecules" *Nature* 350:703–706 (Apr. 25, 1991).

Falk et al., "Allele–specific Motifs Revealed by Sequencing of Self–peptides Eluted from MHC Molecules", *Nature* 351:290–296 (May 23, 1991).

Ferrari et al., "Identification of Immunodominant T Cell Epitopes of the Hepatitis B Virus Nucleocapsid Antigen", *J. Clin. Invest.*, 88:214–222 (Jul. 1991).

Bertoletti, "HLA Class I–restricted Human Cytotoxic T Cells Recognize Endogenously Synthesized Hepatitis B Nucleocapsid Antigen", *Proc. Natl. Aad/ Sci. USA* 88:10445–10449 (Dec. 1991).

Penna et al., "Cytotoxic T Lymphocytes Recognize an HLA–A2–restricted Epitope Within the Hepatitis B Virus Nucleocapsid Antigen", *J. Exp. Med.* 174:1565–1570 (Dec. 1991).

Sarobe et al. "Induction of Antibodies Against Peptide Hapten Does Not Require Covalent Linkage Between Hapten & Class II Presentable T Helper Peptide", *Eur. J. Immunol.* 21:1555–15558 (1991).

Cassell et al., "Linked Recognition of Helper and Cytotoxic Antigenic Determinants for the Generation of Cytotoxic T Lymphocytes", *Ann. N.Y. Acad. Sci.*, pp. 51–60 (1991).

Penna et al., "Hepatitis B Virus HBV–Specific Cytotoxic T Cell (CTL) Response in Humans: Characterization of HLA Class II–Restricted CTLs That Recognize Endogenously Synthesized HBV Envelope Antigens", *J. Virol.* 66:1193–1198 (Feb. 1992).

Guilhot et al., "Hepatitis B Virus (HBV) –Specific Cytotoxic T–Cell Response in Humans: Production of Target Cells by Stable Expression of HBV–Encoded Proteins in Immortalized Human B–Cell Lines", *J. Virol.* 66:2670–2678 (May 1992).

Bhatnagar et al., "Immune Response to Synthetic Peptide Analogues of Hepatitis B Surface Antigen Specific for the Determinant" *Proc. Natl. Acad. Sci. USA* 79:4400–44–4 (Jul. 1982).

Mondelli et al., "Specificity of T Lymphocyte Cytotoxicity to Autologous Hepatocytes in Chronic Hepatitis B Virus Infection: Evidence that T Cells are Directed Against HBV Core Antigen Expressed on Hepatocytes", *J. Immunol.*, 129:2773–2778 (Dec. 1982).

von Boehmer et al., "Autonomously Proliferating K/D–restricted Cytolytic T Cell Clones", *Eur. J. Immunol.* 13:176–179 (1983).

Neurath et al., "Specificity of Antibodies Elicited by a Synthetic Peptide having a Sequence in Common with a Fragment of a Virus Protein —The Hepatitis B Surface Antigen", *Develop. Biol. Standard*, 54:103–112 (1983).

von Boehmer et al., "Lyt–2 Cell–Independent Functions of Lyt–2+ Cells Stimulated with Antigen or Concanavalin A", *J. Immunol.*, 133:59–64 (Jul. 1984).

Hopp, "Immunogenicity of a synthetic HBsAg Peptide: Enhancement by Conjugate to a Fatty Acid Carrier", *Molecular Immunol.* 21:13–16 (1984).

Milich et al., "Immunogenetics and Cellular Correlates of the Immune Response to Hepatitis B Surface Antigen Determinants", *Adv. Hepatitis Res.* Masson, NY, NY USA 91–109 (1984).

Fujii et al., "Peptide Chemistry 1983" published 1984 by Protein Research Foundation (OSAKA), pp. 215–220.

Sprent et al., "Properties of Purified T Cell Subsets", *J. Exp. Med.*, 162:2068–2088 (Dec. 1985).

Townsend et al., "The Epitopes of Influenza Nucleoprotein Recognized by Cytotoxic T Lymphocytes Can Be Defined with Short Synthetic Peptides", *Cell* 44:959–968 (Mar. 28, 1986).

Bessler et al., "The Syntheitc Analog of Bacterial Lipoprotein are Potent Immunoadjuvants in Combination with or Covalently Linked to Antigen", *Prog. Leukocyte Biol.* 5:337–344 (1986).

Watari et al., "A Synthetic Peptide Induces Long –Term Protection from Lethal Infection with Herpes Simplex Virus 2", *J. Exp. Med.*, 165:459–470 (Feb. 1987).

Gotch et al., "Cytotoxic T Lymphocytes Recognize a Fragment of Influenza Virus Matrix Protein in Associate with HLA–A2", *Nature* 326:881–882 (Apr. 30, 1987).

Buller et al., "Induction of Cytotoxic T–Cell Responses in vivo in Absence of CD4 Helper Cells" *Nature* 328:76–79 (Jul. 2, 1987).

Milich et al., "Immune Response to Hepatitis B Virus Core Antigen (HBcAg): Localization of T Cell Recognition Sites Within HBcAg/HBeAg", *J. Immunol.*, 139:1223–1231 (Aug. 15, 1987).

Milich et al., "Antibody Production to the Nucleocapsid and Envelope of the Hepatitis B Virus Primed by a Single Synthetic T Cell Site", *Nature* 329:547–549 (Oct. 8, 1987).

Mondelli et al., "Definition of Hepatitis B Virus (HBV)–specific Target Antigens Recognized by Cytotoxic T Cells in Acute HBV Infection", *Clin. Exp. Immunol.*, 68:242–250 (1987).

Milich et al., "Hepatitis B Synthetic Immunogen Comprised of Nucleocapsid T–cell Sites and an Envelope B–Cell Epitope", *Proc. Natl. Acad. Sci. USA* 85:1610–1614 (Mar. 1988).

Zinkernagel et al., "The Lymphoreticular System in Triggering Virus Plus Self–Specific Cytotoxic T Cells: Evidence for T Help", *J. Exp. Med.*, 147:897–911 (1978).

Galibert et al., "Nucleotide Sequence of the Hepatitis B Virus Genome (subtype ayw) Cloned in *E. Coli* ", *Nature* 281:646–650 (Oct. 25, 1979).

von Boehmer et al., "Distinct Ir Genes for Helper and Killer Cells in the Cytotoxic Response to H–Y Antigen", *J. Exp. Med.*, 150:1134–1142 (Nov. 1979).

Melief et al., "Cooperation Between Subclasses of T Lymphocytes in the in vitro Generation of Cytotoxity Against a Mutant H–2K Difference An Analysis with Anti–Lyt Antisera", *Eur. J. Immunol.* 9:7–12 (1979).

Widmer et al., "Antigen–Driven Helper Cell–independent Cloned Cytolytic T Lymphocytes", *Nature* 294:750–752 (1981).

Lerner et al., "Chemically Synthesized Peptides Predicted form the Nucleotide Sequence of the Hepatitis B Virus Genome Elicit Antibodies Reactive with the Native Envelope Protein of Dane Particles" *Proc. Natl. Acad. Sci. USA* 78:3403–3407 (Jun. 1981).

Mack et al. "Hepatitis B Virus Particles . . . "J. Virology 62:12, pp. 4786–4790, Dec. 1988.

Yssel, H; Johnson, K E ; Schneider, P V; Wideman, J; Terr, A; Kastlelein, R; De Vries, J E; "T cell activation–inducing epitopes of the house dust mite allergen Der p I. Proliferation and lymphokine production patterns by Der p I–specific CD4+ T cell clones," J. Immunol. (1992), 148(3), 738–45.

Lee, K K; Paranchych, W; Hodges, R S, "Cross–reactive and strain–specific antipeptide antibodies to Pseudomonas aeruginosa PAK and PAO pili," Infect. Immun. (1990), 58(9), 2727–32.

Ruppert, J; Sidney, J; Celis, E; Kubo, R T.; Grey, H M.; Sette, A, "Prominant role of secondary anchor residues in peptide binding to HLA–A2.1 molecules," Cell(1993), 74(5), 929–37.

Jameson S C; Carbone F R; Brevan M J, "Clone–specific T cell receptor antagonist of major histocompatibility complex class I–restricted cytoxic T cells," Journal of Experimental Medicine, (Jun. 1, 1993) 177 (6) 1541–50.

Bertoletti A; Sette A; Chisari F V; Penna A; Levrero M; De Carli M; Fiaccadori F; Ferrari C; "Natural variants of cytotoxic epitopes are T–cell receptor antagonists for antiviral cytotoxic T cells," Nature (Jun. 2, 1994) 369: 407–410.

De Magistris M T; Alexander J; Coggeshall M; Altman A; Gaeta F C; Grey H M; Sette A, "Antigen analog–major histocompatibility complexes act as antagonists of the T cell receptor," Cell, (Feb. 21, 1992) 68 (4) 625–34.

Bichko et al., "Subtype ayw variant of hepatitis B virus", FEBS Lett. 185, 208–212 (1985).

Carbone et al., "Induction of Ovalbumin–Specific Cytotoxic T Cells by in vivo Peptide Immunization", J Exp. Med., 169, 603–612 (1989).

Falk et al., "Allele–specific motifs revealed by sequencing of self–peptides eluted from MHC molecules", Nature 351, 290–296 (May 1991).

Ferrari et al., "Identification of Immunodominant T Cell Epitopes of the Hepatitis B Virus Nucleocapsid Antigen", J. Clin. Invest. 88, 214–222 (Jul. 1991).

Deres et al., "In vivo priming of virus–specific cytotoxic T lymphocytes with synthetic lipopeptide vaccine", Nature 342, 561–564 (1989).

Galibert et al., "Nucleotide sequence of the hepatitis B virus genome (subtype ayw) cloned in *E. coli* ", Nature 281, 646–650 (1979).

Mack et al. "Hepatitis B Virus Particles . . . "J. Virology 62:12 pp. 4786–4790, Dec. 1988.

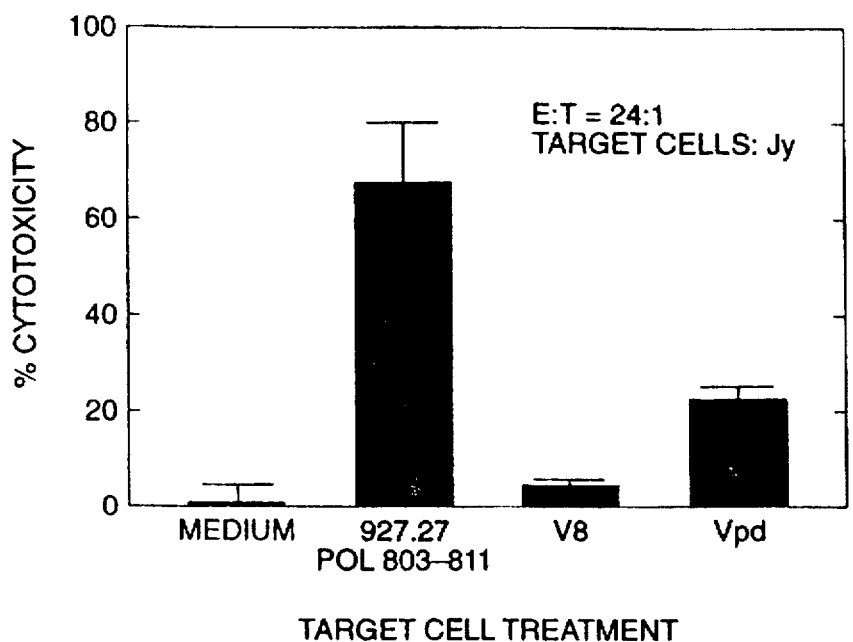
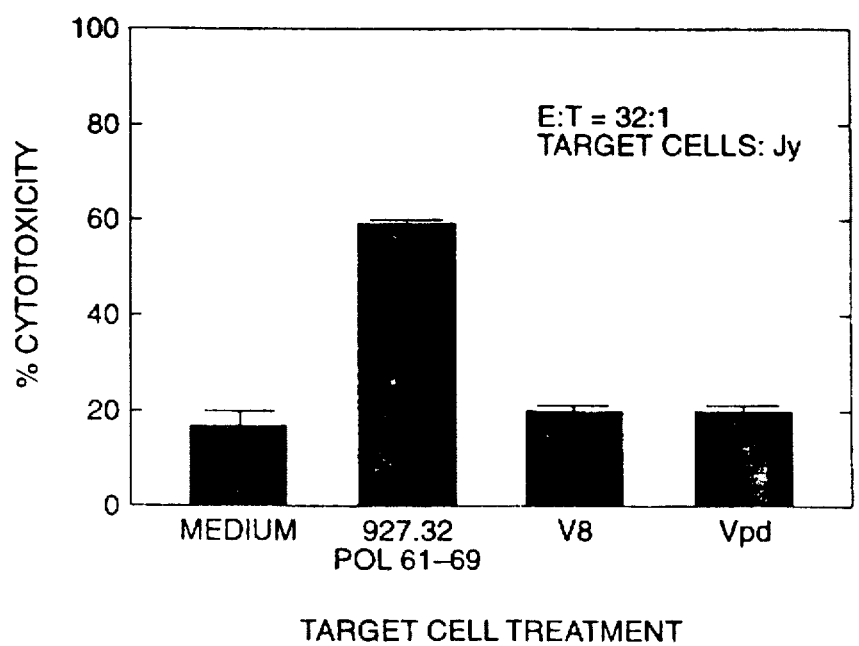
FIG. 3

FIG. 4A

```
     1
 39  MPLSYQHFRKLLLLDD--EA  GPLEEELPRLADEGLNRRVA  EDLNLGNLGNLNVSIPWTHKVGN
 40  MPLSYQHFRKLLLLLD???EA GPLEEELPRLADEGLNRRVA  EDLNLGNLGNLNVSIPWTHKVGN
 41  MPLSYQHFRKLLLLDD--EA  GPLEEELPRLADEGLNRRVA  EDLNLGNLGNLNVSIPWTHKVGN
 42  MPLSYQHFRKLLLLDD--EA  GPLEEELPRLADEGLNRRVA  EDLNLGNLGNLNVSIPWTHKVGN
 43  MPLSYQHFRKLLLLDD--EA  GPLEEELPRLADEGLNRRVA  EDLNLGNLGNLNVSIPWTHKVGN
 44  MPLSYQHFRKLLLLDD--EA  GPLEEELPRLADEGLNRRVA  EDLNLGNLGNLNVSIPWTHKVGN
 45  MPLSYQHFRKLLLLDD--EA  GPLEEELPRLADEDLNRRVA  EDLNLGNLGNLNVSIPWTHKVGN
 46  MPLSYQHFRKLLLLDD--EA  GPLEEELPRLADADLNRRVA  EDLNLGNLGNLNVSIPWTHKVGN
 47  MPLSYQHFRKLLLLDDGTEA  GPLEEELPRLADEGLNHRVA  EDLNLGNPNVSIPWTHKVGN
 48  MPLSYQHFRKLLLLLDE--EA GPLEEELPRLADEGLNRRVA  EDLNLGNLGNLNVSIPWTHKVGN
 49  MPLSYQHFRKLLLLDD--EA  GPLEEELPRLADEGLNRRVA  EDLNLGNLGNLNVSIPWTHKVGN
 50  MPLSYQHFRKLLLLLDDGTEA GPLEEELPHLADEGLNRPVA  EDLNLGNLGNLNVSIPWTHKVGN
 51  MPLSYQHFRKLLLLLDD--EA GPLEEELPRLADEGLNRPVA  EDLNLGNLGNLNVSIPWTHKVGN
 52  MPLSYQHFRKLLLLLDDGTEA GPLEEELPRLADADLNRRVA  EDLNLGNLGNLNVSIPWTHKVGN
 53  MPLSYQHFRKLLLLDD--EA  GPLEEELPRLADADLHRRVA  EDLNLGNLGNLNVSIPWTHKVGN
 54  MPLSYQHFRKLLLLDD--EA  GPLEEELPRLADEGLNRRVA  EDLNLGNLGNLNVSIPWTHKVGN
 55  MPLSYQHFRRLLLLDD--EA  GPLEEELPRLADEGLNRRVA  EDLNLGNLGNLNVSIPWTHKVGN
 56  MPLSYQHFRRLLLLDD--EA  GPLEEELPRLADEGLNRRVA  EDLNLGNLGNLNVSIPWTHKVGN
 57  MPLSYQHFRRLLLLDD--EA  GPLEEELPRLADEGLNRRVA  EDLNLGNLGNLNVSIPWTHKVGN
 58  MPLSYQHFRRLLLHD--EA   GPLEEELPRLPDQGLNRRVA  EDLNLGNLGNLNVSIPWTHKVGN
158  MPLSYQHFRkLLLLddGTEA  GPLEEELPrLaDegLnrrVA  EDLNLGNlNVSIPWTHKVGN
```

FIG. 4B

```
     61
 39  FTGLYSSTVPVFNPEWQTPS  FPHIHLQEDIINRCQQYVGP  LTVNEKRRLKLIMPARFYPN
 40  FTGLYSSTVPIFNPEWQTPS  FPHIHLQEDIINRCQQYVGP  LTVNEKRRLKLIMPARFYPN
 41  FTGLYSSTVPVLNPESQTPS  FPNIHLQEDIINRCQQYVGP  LTVNEKRRLKLIMPARFYPN
 42  FTGLYSSTVPVFNPEWQTPS  FPNIHLQEDIINRCQQYVGP  LTVNEKRRLKLIMPARFYPN
 43  FTGLYSSTVPVFNPEWQTPS  FPHIHLQEDIINRCQQYVGP  LTVNEKRRLKLIMPARFYPN
 44  FTGLYSSTVPVFNPEWQTPS  FPHIHLQEDIINRCQQYVGP  LTVNEKRRLKLIMPARFYPN
 45  FTGLYSSTVPVFNPEWQTPS  FPHIHLQEDIINRCQQYVGP  LTVNEKRRLKLIMPARFYPK
 46  FTGLYSSTVPIFNPEWQTPS  FPKIHLQEDIINRCQQYVGP  LTVNEKRRLKLIMPARFYPT
 47  FTGLYSSTVPVFNPEWQTPS  FPDIHLQEDIVDRCKQFVGP  LTVNENRRLKLIMPARFYPN
 48  FTGLYSSTVPCFNPKWQTPS  FPDIHLQEDIVDRCKQFVGP  LTVNENRRLKLIMPARFYPN
 49  FTGLYSSTVPSFNPKWQTPS  FPDIHLQEDIINKCKQFVGP  LTVNEKRRLKLIMPARFYPN
 50  FTGLYSSTVPSFNPKWQTPS  FPDIHLQEDIINRCEQFVGP  LTVNENRRLKLIMPARFYPT
 51  FTGLYSSTAPIFNPEWQTPS  FPKIHLQEDIINRCQQFVGP  LTVNEKRRLKLIMPARFYPT
 52  FTGLYSSTVPIFNPEWQTPS  FPKIHLQEDIINRCQQFVGP  LTVNEKRRLKLIMPARFYPN
 53  FTGLYSSTVPIFNPEWQTPS  FPHIHLQEDIINRCQQYVGP  LTVNEKRRLKLIMPARFYPN
 54  FTGLYSSTVPVFNPHWKTPS  FPNIHLHQDIIKKCEQFVGP  LTVNEKRRLQLIMPARFYPK
 55  FTGLYSSTVPVFNPHWKTPS  FPNIHLHQDIIKKCEQFVGP  LTVNEKRRLQLIMPARFYPK
 56  FTGLYSSTVPVFNPHWKTPS  FPNIHLHQDIIKKCEQFVGP  LTVNEKRRLQLIMPARFYPK
 57  FTGFYSSTVPVFNPHWETPS  FPNIHLHQDIIKKCEQFVGP  LTVNEKRRLQLIMPARFYPN
 58  FTGLYSSTVPVFNPHWKTPS  FPNIHLHQDIIKKCEQFVGP  LTVNEKRRLQLIMPARFYPN
158  FTGlYSSTvPvfNPewqTPS  FP.IHLqeDIinrCqQFVGP  LTVNEkRRLKLIMPARFYPn
```

FIG. 4C

```
     121
 39  LTKYLPLDKGIKPYYPEHAV  NHYFKTRHYLHTLWKAGILY  KRETTRSASFCGSPYSWEQE
 40  LTKYLPLDKGIKPYYPEHAV  NHYFKTRHYLHTLWKAGILY  KRETTRSASFCGSPYSWEQE
 41  LTKYLPLDKGIKPYYPEHAV  NHYFKTRHYLHTLWKAGILY  KRETTRSASFCGSPYSWEQE
 42  LTKYLPLDKGIKPYYPEHAV  NHYFKTRHYLHTLWKAGILY  KRETTRSASFCGSPYSWEQE
 43  LTKYLPLDKGIKPYYPEHAV  NHYFKTRHYLHTLWKAGILY  KRETTRSASFCGSPYSWEQE
 44  LTKYLPLDKGIKPYYPEHAV  NHYFKTRHYLHTLWKAGILY  KRETTRSASFCGSPYSWEQE
 45  LTKYLPLDKGIKPYYPEHAV  NHYFKTRHYLHTLWKAGILY  KRETTRSASFCGSPYSWEQE
 46  HTKYLPLDKGIKPYYPDQVV  NHYFQTRHYLHTLWKAGILY  KRESTRSASFCGSPYSWEQD
 47  VTKYLPLDKGIKPYYPEHVV  NHYFQTRHYLHTLWKAGILY  KRETTRSASFCGSPYSWEQE
 48  VTKYLPLDKGIKPYYPEYVV  NHYFQTRHYLHTLWKAGILY  KRETTRSASFCGSPYSWEQE
 49  VTKYLPLDKGIKPYYPEHVV  NHYFQTRHYLHTLWKAGILY  KRETTRSASFCGSPYSWEQE
 50  VTKYLPLDKGIKPYYPDQVV  NHYFKTRHYLHTLWKAGILY  KRETTRSASFCGSPYSWEQE
 51  HTKYLPLDKGIKPYYPDQVV  NHYFQTRHYLHTLWKAGILY  KRETTRSASFCGSPYSWEQE
 52  HTKYLPLDKGIKPYYPDQVV  NHYFQTRHYLHTLWKAGILY  KRETTRSASFCGSPYSWEQE
 53  LTKYLPLDKGIKPYYPEYAV  NHYFKTRHYLHTLWKAGILY  KRETTRSASFCGSPYSWEQE
 54  VTKYLPLDKGIKPYYPEHLV  NHYFKTRHYLHTLWKAGILY  KRETTHSASFCGSPYSWEQD
 55  VTKYLPLDKGIKPYYPEYLV  NHYFQTRHYLHTLWKAGILY  KRETTHSASFCGSPYSWEQD
 56  VTKYLPLDKGIKPYYPEHLV  NHYFQTRHYLHTLWKAGILY  KRETTHSASFCGSPYSWEQD
 57  VTKYLPLDKGIKPYYPEHLV  NHYFQTRHYLHTLWKAGILY  KRETTHSASFCGSPYSWEQD
 58  VTKYLPLDKGIKPYYPEHLV  NHYFQTRHYLHTLWKAGILY  KRETTHSASFCGSPYSWEQD
158  .TKYLPLDKGIKPYYPeh.V  NHYFqTRHYLHTLWKAGILY  KREtTrSASFCGSPYSWEQe
```

FIG. 4D

```
     181
39   LQHGRLVFQTSTRHGDESFC  SQSSGILSRSPVGPCVRSQL  KQSRLGLQPQQGSMARGKSG
40   LQHGRLVFQTSTRHGDESFC  SQSSGILSRSPVGPCVRSQL  KQSRLGLQPQQGSLARGKSG
41   LRHGRLVFQTSTRHGDESFC  SQSSGILSRSPVGPCVRSQL  KQSRLGLQPQQGSLARGNQG
42   LQHGRLVFQTSTRHGDESFC  SQSSGILSRSPVGPCIRSQL  KQSRLGLQPQQGSLARGKSG
43   LQHGRLVFQTSTRHGDESFC  SQSSGILSRSPVGPCVRSQL  TQSRLGLQPQQGSLARGKSG
44   LQHGRLVFQTSTRHGDESFC  SQSSGILSRSPVGPCVRSQL  KQSRLGLQPQQGSLARGKSG
45   LQHGRLVFQTSTRHGDESFC  SQSSGILSRSPVGPCVRSQL  KQSRLGLQPQQGSLARGKSG
46   LQH-------SQRHGDESFC  SQPSGIPSRSSVGPCIRSQL  NKSRLGLQPHQGPLASSQPG
47   LQHGRLVFQTSKRHGDKSFC  PQSPGILPRSSVGPCIQSQL  RKSRLGPQPTQGLAGRPQG
48   LQHGRLVFQTSKRHGDKSFC  PQSSGILPRSSVGPCIQSQL  RKSRLGPQPEQGLAGRQQG
49   LQHGRLVLQTSTRHGDKSFR  PQSSGILSRSPVGPCIQSQL  RQSRLGPQPTQGLAGLQQG
50   LQHGRLVLQTSTRHGDKSFR  PQSSGILSRSPVGPCIQSQL  RQSRLGPQPTQGLAGLQQG
51   LQHGRLVIKTSQRHGDESFC  SQPSGILSRSSVGPCIRSQL  KQSRLGLQPHQGPLASSQPG
52   LQHGRLVIKTSCRHGDESFC  SQSSGILSRSPVGPCIRSQL  KQSRLGLQPRQGRLASSQPS
53   LQHGRLVFQTSTRHGDESFC  SQSSGILSRSPVGPCVRSQL  KQSRLGLQPQQGSLARGKSG
54   LQHG----------AESFH  QQSSGILSRPPVGSSLQSKH  RKSRLGLQSQQGHLARRQQG
55   LQHG----------AESFH  QQSSGILSRPPVGSSLQSKH  RKSRLGLQSQQGHLARRQQG
56   LQHG----------AESFH  QQSSGILSRPPVGSSLQSKH  RKSRLGLQSQQGHLARRQQG
57   LQHG----------AESIH  QQSSGILSRPPVGSSLQSKH  RKSRLGLQSQQGHLARRQQG
58   LQHG----------AESFH  QQSSGILSRPPVGSSLQSKH  RKSRLGLQSQQGHLARRQQG
158  LqHGRLVfqTStRHGdeSfc  sQssGIlsRspVGpc.rSql  .qSRLGlQpqQG.lAr.qqg
```

FIG. 4E

```
    241
39   RSGSIRARVHPTTRRSFGVE   PSGSGHIDNSASSTSSCLHQ   SAVRKTAYSHLSTSKRQSSS
40   RSGSIRARVHPTTRRSFGVE   PSGSGHIDNSASSTSSCLHQ   SAVRKTAYSHLSTSKRQSSS
41   RSGRLRARVHPTTRRSFGVE   PSGSGHIDNSASSASSCFHQ   SAVRKTAYSHLSTSKRQSSS
42   RSGSIWARVHSTTRRSFGVE   PSGSGHIDNSASSASSCLYQ   SAVRKTAYSHLSTSKRQSSS
43   RSGSIRARVHPTTRRSFGVE   PAGSGRIDNRASSTSSCLHQ   SAVRKTAYSHLSTSKRQSSS
44   RSGSIRARVPPTTRRSFGVE   PSGSGHIDNRASSTSSCLHQ   SAVRKTAYSHLSTSKRQSSS
45   RSGSIRARVPPTTRRSFGVE   PSGSGHIDNRASSTSSCLHQ   SAVRKTAYSHLSTSKRQSSS
46   RSGSIRARAHPSTRRYFGVE   PSGSGHIDHSVNNSSSSCLHQ  SAVRKAAYSHLSTSKRQSSS
47   GSGSIRARIHPSPWGTVGVE   PSGSGHTHICASSSSSSCLHQ  SAVRTAAYSPISTSKGHSSS
48   GSGSIRARVHPSPWGTVGVE   PSGSGPTHNCASSSSSSCLHQ  SAVRKAAYSLIPTSKGHSSS
49   GSGSIRAGIHSTPWGTVGVE   PSSSGHTHNCANSSSSSCLHQ  SAVRKEAYSPVSTSKRHSSS
50   GSGSIRAGIHSTPWGTVGVE   PSSSGHTHNCANSSSSSCLHQ  SAVRKEAYSPVSTSKRHSSS
51   RSGSIRARVHPSTRRCFGVE   PSGSGHVDPSVNNSSSCLRQ   SAVRKAAYSHLSTSKRQSSS
52   RSGSIRAKAHPSTRRYFGVE   PSGSGHIDHSVNNSSSSCLHQ  SAVRKAAYSHLSTSKRQSSS
53   RSGSIWSRVHPTTRRPFGVE   PSGSGHIDNTASSTSSCLHQ   SAVRKTAYSHLSTSKRQSSS
54   RSWSIRAGFHPTARRPFGVE   PSGSGHTTNFASKSASCLHQ   SPVRKAAYPAVSTFEKHSSS
55   RSWSIRAGIHPTTRRPFGVE   PSGSGHTTNFASKSASCLYQ   SPVRKAAYPAVSTFEKHSSS
56   RSWSIRAGFHPTARRPFGVE   PSGSGHTRNVASKSASCLYQ   SPVRKAAYPSVSTFEKHSSS
57   WSWSIRAGTHPTARRPFGVE   PSGSGHTTHRASKSASCLYQ   SPDRKATYPSVSTFERHSSS
58   RSWSIRAGFHPTARRSFGVE   PSGSGHTTYRASKSASCLYQ   SPVRKAAYPSVSTFEKHSSS
158  rSgsirarvhpttrr.fGVE   PsgSGhidn.asssssClhQ   SavRkaaYshlsTskrqSSS
```

FIG. 4F

```
     301
39   GHAVEFHNIPPSSARSQSEG   PIFSCWWLQFRNSKPCSDYC   LTHIVNLLEDWGPCTEHGEH
40   GHAVELHNIPPSSARPQSEG   PILSCWWLQFRNSKPCSDYC   LTHIVNLLEDWGPCTEHGEH
41   GHAVELHNIPPSSARSQSEG   PIFSCWWLQFRNSKPCSDYC   LTHIVNLLEDWGPCTEHGEH
42   GHAVELHNIPPSSCARSQSEG  PISSCWWLQFRNSEPCSDYC   LTHIVNLLEDWGPCTEHGEH
43   GHAVELHNIPPSSARPQSEG   PILSCWWLQFRNSKPCCDYC   LTHIVNLLEDWGPCTEHGEH
44   GHAVELHHISPSPARSQSEG   PIFSSWWLQFRNSKPCSDYC   LTHIVNLLEDWGPCTEHGEH
45   GHAVELHHISPSPARSQSEG   PIFSSWWLQFRNSKPCSDYC   LTHIVNLLEDWGPCTEHGEH
46   GHAVEFHCLAPSSAGSQSQG   SVSSCWWLQFRNSKPCSEYC   LSHLVNLREDWGPCDDHGEH
47   GHAVELHHFPPNSSRSRSQSQG GNAVLSCWWLQFRNSKPCSEYC LSHIVNLIEDWGPCAEHGEH
48   GHAVELHHFPPNSSRSRSQSQG PVLSCWWLQFRNSEPCSEYC   LCHIVNLIEDWGPCTEHGEH
49   GNAVELHHVPPNSSRSQSQG   SVLSCWWLQFRNSKPCSEHC   LFHIVNLIDDWGPCAEHGEH
50   GHAVELHHVPPNSSRSQSQG   SVLSCWWLQFRNSKPCSEYC   LFHIVNLIEDWGPCAEHGEH
51   GHAVEFHCLPPSSARPQSQG   SVFSCWWLQFRNSKPCSEYC   LSHLVNLREDRGPCDEHGEH
52   GHAVEFHCLPPNSAGSQSQG   SVSSCWWLQFRNSKPCSEYC   LSHLVNLREDWGPCDEHGEH
53   GHAVELHNIPPSSARSQSER   PIFSCWWLQFRNSKPCSDYC   LTHIVNLLEDWGPCTEHGEH
54   GHAVEFHNLPPNSARSQSER   PVFPCWWLQFRNSKPCSDYC   LSIVNLLEDWGPCAEHGEH
55   GHAVELHNLPPNSARSQSER   PVFPCWWLQFRNSKPCSDYC   LSHIVNLLEDWGPCAEHGEH
56   GHAVELHNLPPNSARSQSER   PVFPCWWLQFRNSKPCSDYC   LSLIVNLLEDWGPCAEHGEH
57   GRAVELHNFPPNSARSQSER   PIFPCWWLQFRNSKPCSDYC   LSLIVNLLEDWGPCDEYGEH
58   GHAVELHNLPPNSARSQSER   PVFPCWWLQFRNSKPCSDYC   LSLIVNLREDWGPCTEHGEH
158  GhAVElHn.pPnsarsqSeg   pvfscWWLQFRNSkPCsdyC   L.hiVNLleDwGPCtehGEH
```

FIG. 4G

```
    361
39  NIRIPRTPARVTGGVFLVDK  NPHNTTESRLVVDFSQFSRG  STHVSWPKFAVPNLQSLTNL
40  NIRIPRTPARVTGGVFLVDK  NPHNTTESTLVVDFSQFSRG  STHVSWPKFAVPNLQSLTNL
41  NIRIPRTPARVTGGVFLVDK  NPHNTTESRLVVDFSQFSRG  STHVSWPKFAVPNLQSLTNL
42  NIRIPRTPARVTGGVFLVDK  NPHNTTESRLVVDFSQFSRG  STHVSWPKFAVPNLQSLTNL
43  NIRIPRTPARVTGGVFLVDK  NPHNTTESRLVVDFSQFSRG  STHVSWPKFAVPNLQSLTNL
44  NIRIPRTPARVTGGVFLVDK  NPHNTTESRLVVDFSQFSRG  STHVSWPKFAVPNLQSLTNL
45  NIRIPRTPARVTGGVFLVDK  NPHNTAESRLVVDFSQFSRG  STHVSWPKFAVPNLQSLTNL
46  HIRIPRTPARVTGGVFLVDK  NPHNTTESRLVVDFSQFSRG  ITRVSWPKFAVPNLQSLTNL
47  RIRTPRTPARVTGGVFLVDK  NPHNTAESRLVVDFSQFSRG  NTRVSWPKFAVPNLQSLTNL
48  RIRTPRTPARVTGGVFLVDK  NPHNTAESRLVVDFSQFSRG  NTRVSWPKFAVPNLQSLTNL
49  RIRTPRTPARVTGGVFLVDK  NPHNTAESRLVVDFSQFSRG  NTRVSWPKFAVPNLQSLTNL
50  RIRTPRTPARVTGGVFLVDK  NPHNTAESRLVVDFSQFSRG  NTRVSWPKFAVPNLQSLTNL
51  HIRIPRTPARVTGGVFLVDK  NPHNTAESRLVVDFSQFSRG  ITRVSWPKFAIPNLQSLTNL
52  HIRIPRTPARVTGGVFLVDK  NPHNTAESRLVVDFSQFSRG  ISRVSWPKFAVPNLQSLTNL
53  NIRIPRTPARVTGGVFLVDK  NPHNTSESRLVVDFSQFSRG  STHVSWPKFAVPNLQSLTNL
54  HIRIPRTPSRVTGGVFLVDK  NPHNTAESRLVVDFSQFSRG  NYRVSWPKFAVPNLQSLTNL
55  HIRIPRTPARVTGGVFLVDK  NPHNTAESRLVVDFSQFSRG  NYRVSWPKFAVPNLQSLTNL
56  HIRIPRTPSRVTGGVFLVDK  NPHNTAESRLVVDFSQFSRG  NYRVSWPKFAVPNLQSLTNL
57  HIRIPRTPARVTGGVFLVDK  NPHNTAESRLVVDFSQFSRG  NYRVSWPKFAVPNLQSLTNL
58  HIRIPRTPARVTGGVFLVDK  NPHNTAESRLVVDFSQFSRG  NYRVSWPKFAVPNLQSLTNL
158 .IRiPRTPaRVTGGVFLVDK  NPHNTtESrLVVDFSQFSRG  .trVSWPKFAvPNLQSLTNL
```

FIG. 4H

```
    421
39  LSSNLSWLSLDVSAAFYHIP  LHPAAMPHLLLVGSSGLPRYV  ARLSSTSRNINHQHGAMQDL
40  LSSNLSWLSLDVSAAFYHIP  LHPAAMPHLLLVGSSGLPRYV  VCLSSTSRNINYQHGTMQDL
41  LSSNLSWLSLDVSAAFYHIP  LHPAAMPHLLLVGSSGLPRYV  ARLSSTSRNINYQHGTMQDL
42  LSSNLSWLSLDVSAAFYHIP  LHPAAMPHLLLVGSSGLPRYV  ARLSSTSRNINYQHGTMQDL
43  LSSNLSWLSLDVSAAFYHIP  LHPAAMPHLLLVGSSGLPRYV  ARLSSTSRNINYQHGTMQDL
44  LSSNLSWLSLDVSAAFYHIP  LHPAAMPHLLLVGSSGLPRYV  ARLSSTSRNINHQHGTMQDL
45  LSSNLSWLSLDVSAAFYHIP  LHPAAMPHLLLVGSSGLPRYV  ARLSSTSRNINHQHGTMQDL
46  LSSNLSWLSLDVSAAFYHIP  LHPAAMPHLLLIGSSGLSRYV  ARLSSNSRINNNQYGTMQNL
47  LSSNLSWLSLDVSAAFYHLP  LHPAAMPHLLLVGSSGLSRYV  ARLSSNSRIINHQHGTMQNL
48  LSSNLSWLSLDVSAAFYHLP  LHPAAMPHLLLVGSSGLSRYV  ARLSSNSRIINNQHRTMQNL
49  LSSDLSWLSLDVSAAFYHIP  LHPAAMPHLLLVGSSGLSRYV  ARLSSNSRIINHQHRTMQNL
50  LSSDLSWLSLDVSAAFYHIP  LHPAAMPHLLLVGSSGLSRYV  ARLSSNSRINNNQYGTMQNL
51  LSSNLSWLSLDVSAAFYHLP  LHPAAMPHLLLIGSSGLSRYV  ARLSSNSRINNNQYGTMQNL
52  LSSNLSWLSLDVSAAFYHIP  LHPAAMPHLLLVGSSGLPRYV  ARLSSTSRNINYQHGTMQNL
53  LSSNLSWLSLDVSAAFYHIP  LHPAAMPHLLLVGSSGLSRYV  ARLSSNSRILNNQHGTMPDL
54  LSSNLSWLSLDVSAAFYHLP  LHPAAMPHLLLVGSSGLSRYV  ARLSSNSRIFNYQHGTMQNL
55  LSSNLSWLSLDVSAAFYHLP  LHPAAMPHLLLVGSSGLSRYV  ARLSSNSRILNHQHGTMQNL
56  LSSNLSWLSLDVSAGFYHLP  LHPAAMPHLLLVGSSGLSRYV  ARLSSNSRILNHQHGTMPNL
57  LSSNLSWLSLDVSAAFYHLP  LHPAAMPHLLLVGSSGVSRYV  ARLSSNSRINNNQYGTMQNL
58  LSSNLSWLSLDVSAAFYHLP  LHPAAMPHLLLVGSSGLSRYV  ARLSSNSRIFNNQHGTMQNL
158 LSSnLSWLSLDVSAaFYHiP  LHPAAMPHLLvGSSGlsRYV  arLSSnSriiN.QhgtMqnL
```

FIG. 4I

```
    481
39  HDSCSRNLYVSLLLLYKTFG  RKLHLYSHPIILGFRKIPMG  VGLSPFLLAQFTSAICSVVR
40  HDSCSRNLYVSLFLLYKTFG  RKLHLYSHPIILGFRKIPMG  VGLSPFLLAQFTSAICSVVR
41  HDSCSRNLYVSLLLLYKTFG  RKLHLYSHPIILGFRKIPMG  VGLSPFLLAQFTSAICSVVR
42  HDSCSRNLYVSLLLLYKTFG  RKLHLYSHPIILGFRKIPMG  VGLSPFLLAQFTSAICSVVR
43  HDSCSRNLYVSLLLLYKTFG  RKLHLYSHPIILGFRKIPMG  GGLSPFLLAQFTSAICSVVR
44  HDSCSRNLYVSLLLLYKTFG  RKLHLYSHPIILGFRKIPMG  GGLSPFLLAQFTSAICSVVR
45  HDSCSRNLYVSLLLLYKTFG  RKLHLYSHPIILGFRKIPMG  GGLSPFLLAQFTSAICSVVR
46  HDSCSRQL
47  HNSCSRNLYVSIMLLYKTYG  WKLHLYSHPIILGFRKIPMG  VGLSPFLLAQFTSAICSVVR
48  HNSCSRNLYVSIMLLYKTYG  WKLHLYSHPIILGFRKIPMG  VGLSPFLLAQFTSAICSVVR
49  HDSCSRNLYVSIMLLYKTYG  RKLHLYSHPIILGFRKIPMG  VGLSPFLLAQFTSAICSVVR
50  HDSCSRNLYVSIMLLYKTYG  RKLHLYSHPIILGFRKIPMG  VGLSPFLLAQFTSAICSVVR
51  HDSCSRQLYVSIMLLYKTYG  WKLHLYSHPIVLGFRKIPMG  VGLSPFLLAQFTSAICSVVR
52  HDSCSRQLYVSIMLLYKTYG  WKLHLYSHPIVLGFRKIPMG  VGLSPFLLAQFTSAICSVVR
53  HDSCSRNLYVSLLLLYKTFG  RKLHLYSHPIILGFRKIPMG  VGLSPFLLAQFTSAICSVVR
54  HDYCSRNLYVSLLLLYQTFG  RKLHLYSHPIILGFRKIPMG  VGLSPFLLAQFTSAICSVVR
55  HDSCSRNLYVSLLLLYQTFG  RKLHLYSHPIILGFRKIPMG  VGLSPFLLAQFTSAICSVVR
56  HDSCSRQLYVSIMLLYQNFG  WKLHLYSHPIVLGFRKIPMG  VGLSPFLLAQFTSAICSVVR
57  HDSCSRNLYVSLLLLYQTFG  RKLHLYSHPIILGFRKIPMG  VGLSPFLLAQFTSAICSVVR
58  HdsCSRnlYVSLlllYktfG  rKLHLYSHPIilGFRKIPMG  vGLSPFLLAQFTSAICSVVR
158
```

FIG. 4J

```
     541
 39  RAFPHCLAFSYMDDVVLGAK  SVQHLESLFTSITNFLLSLG  IHLNPNKTKRWGYSLNFMGY
 40  RAFPHCLAFSYMDDVVLGAK  SVQHLESLFTSITNFLLSLG  IHLNPNKTKRWGYSLNFMGY
 41  RAFPHCLAFSYMDDVVLGAK  SVQHLESLFTSITNFLLSLG  IHLNPNKTKRWGYSLNFMGY
 42  RAFPHCLAFSYMDDVVLGAK  SVQHLESLFTSITNFLLSLG  IHLNPHKTKRWGYSLNFMGY
 43  RAFPHCLAFSYMDDVVLGAK  SVQHLESLFTSITNFLLSLG  IHLNPNKTKRWGYSLNFMGY
 44  RAFPHCLAFSYMDDVVLGAK  SVQHLESLFTSITNFLLSLG  IHLNPNKTKRWGYSLNFMGY
 45  RAFPHCLAFSYMDDVVLGAK  SVQHLESLFTSITNFLLSLG  IHLNPNKTKRWGYSLNFMGY
 47  RAFPHCLAFSYMDDVVLGAK  SVQHLESLYAAVTNFLLSLG  IHLNPNKTKRWGYSLNFMGY
 48  RAFPHCLAFSYMDDVVLGAK  SVQHLESLYAAVTNFLLSLG  IHLNPHKTKRWGYSLNFMGY
 49  RAFPHCLAFSYMDDMVLGAK  SVQHLESLYAAVTNFLLSLG  IHLNPQKTKRWGYSLNFMGY
 50  RAFPHCLAFSYMDDVVLGAK  SVQHLESLYAAVTNFLLSLG  IHLNPNKTKRWGYSLNFMGY
 51  RAFPHCLAFSYMDDVVLGAK  SVQHREFLYTAVTNFLLSLG  IHLNPQKTKRWGYSLNFMGY
 52  RAFPHCLAFSYMDDVVLGAK  SVQHRESLYTAVTNFLLSLG  IHLNPNKTKRWGYSLNFMGY
 53  RAFPHCLAFSYMDDVVLGAK  SVQHLESLFTSITNFLLSLG  IHLNPNKTKRWGYSLNFMGY
 54  RAFPHCLAFSYMDDVVLGAK  SVQHLESLFTAVTNFLLSLG  IHLNPNKTKRWGYSLHFMGY
 55  RAFPHCLAFSYMDDVVLGAK  SVQHLESLFTAVTNFLLSLG  IHLNPNKTKRWGYSLHFMGY
 56  RAFPHCLAFSYMDDVVLGAK  SVQHLESLFTAVTNFLLSLG  IHLNPNKTKRWGYSLNFMGY
 57  RAFPHCLAFSYMDDVVLGAK  SVQHLESLFTAVTNFLLSLG  IHLNPNKTKRWGYSLNFMGY
 58  RAFPHCLAFSYMDDVVLGAK  SVQHlEsLftavTNFLLSLG  IHLNPNKTKRWGYSLNFMGY
158  RAFPHCLAFSYMDDvVLGAK  SVQH1EsLftavTNFLLSLG  IHLNPnKTKRWGYSLnFMGY
```

FIG. 4K

```
    601
39   VIGSWGTLPQEHIVLKLKQC  FRKLPVNSPIDWKVCQRIVG  LLGFAAPFTQCGYPALMPLY
40   VIGCWGTLPQEHIVLKIKQC  FRKLPVNRPIDWKVCQRIVG  LLGFAAPFTQCGYPALMPLY
41   VIGCWGTLPQEHIVLKLKQC  FRKLPVNRPIDWKVCQRIVG  LLGFAAPFTQCGYPALMPLY
42   VIGSWGTLPQEHIVLKIKQC  FRKLPVNRPIDWKVCQRIVG  LLGFAAPFTQCGYPALMPLY
43   VIGCWGTLPQEHIVLKIKQC  FRKLPVNRPIDWKVCQRIVG  LLGFAAPFTQCGYPALMPLY
44   VIGSWGTLPQEHIVLKIKQC  FRKLPVNRPIDWKVCQRIVG  LLGFAAPFTQCGYPALMPLY
45   VIGSWGTLPQEHIVLKIKQC  FRKLPVNRPIDWKVCQRIVG  LLGFAAPFTQCGYPALMPLY
47   VIGSWGTLPQEHIVQNFKLC  FRKLPVNRPIDWKVCQRIVG  LLGFAAPFTQCGYPALMPLY
48   VIGSWGTWPQDHIVQNFKLC  FRKLPVNRPIDWKVCQRIVG  LLGFAAPFTQCGYPALMPLY
49   VIGSWGTLPQEHIVLKIKQC  FRKLPVNRPIDWKVCQRIVG  LLGFAAPFTQCGYPALMPLY
50   VIGSWGTLPQEHIVLKLKQC  FRKLPVNRPIDWKVCQRIVG  LLGFAAPFTQCGYPALMPLY
51   IIGSWGTLPQDHIVQKIKHC  FRKLPVNRPIDWKVCQRIVG  LLGFAAPFTQCGYPALMPLY
52   VIGSWGTLPQEHIVQKLKQC  FRKLPVNRPIDWKVCQRIVG  LLGFAAPFTQCGYPALMPLY
53   VIGCYGSLPQEHIIQKIKEC  FRKLPINRPIDWKVCQRIVG  LLGFAAPFTQCGYPALMPLY
54   VIGCYGSLPQEHIIQKIKEC  FRKLPVNRPIDWKVCQRIVG  LLGFAAPFTQCGYPALMPLY
55   VIGCYGSLPQEHIIQKIKEC  FRKVPVNRPIDWKVCQRIVG  LLGFAAPFTQCGYPALMPLY
56   VIGCYGSLPQEHIIQKIKEC  FRKLPVNRPIDWKVCQRIVG  LLGFAAPFTQCGYPALMPLY
57   IIGSWGTLPQDHIVQKIKEC  FRKLPVNRPIDWKVCQRIVG  LLGFAAPFTQCGYPALMPLY
158  vIGswGtlPQeHIvqkiKqc  FRKlpvNrPIDWKVcQRiVG  LLGFAAPFTQCGYPALMPLY
```

FIG. 4L

```
     661
39   ACIQSKQAFTFSPTYKAFLC   KQYLNLYPVARQRSGLCQVF   ADATPTGWGLAIGHRRMRGT
40   ACIQSKQAFTFSPTYKAFLC   KQYLNLYPVARQRSGLCQVF   ADATPTGWGLAIGHRRMRGT
41   ACIQSKQAFTFSPTYKAFLC   QQYLHLYPVARQRSGLCQVF   ADATPTGWGLAIGHRRMRGT
42   ACIQSKQAFTFSPTYKAFLC   KQYLHLYPVARQRSGLCQVF   ADATPTGWGLAIGQSRMRGT
43   ACIQSKQAFTFSPTYKAFLC   KQYLNLYPVARQRSGLCQVF   ADATPTGWGLAIGHSRMRGP
44   ACIQSKQAFTFSPTYKAFLC   KQYLHLYPVAR-RTALCQVF   ADATPTGWGLAIGHRRMRGT
45   ACIQSKQAFTFSPTYKAFLC   KQYLHLYPVAR-RTALCQVF   ADATPTGWGLAIGHRRMRGT
47   ACIQAKQAFTFSPTYKAFLS   KQYMTLYPVARQRPGLCQVF   ADATPTGWGLAIGHQRMRGT
48   ACIQAKQAFTFSPTYKAFLT   KQYLNLYPVARQRPGLCQVF   ADATPTGWGLAIGHQRMRGT
49   ACIQAKQAFTFSPTYKAFLN   KQYLNLYPVARQRPGLCQVF   ADATPTGWGLAIGHQRMRGT
50   ACIQAKQAFTFSPTYKAFLT   KQYLNLYPVARQRPGLCQVF   ADATPTGWGLAIGHQRMRGT
51   ACIQAKQAFTFSPTYKAFLS   KQYMNLYPVARQRSGLCQVF   ADATPTGWGLAIGHQRMRGT
52   ACIQAKQAFTFSPTYKAFLS   KQYMNLYPVARQRSGLCQVF   ADATPTGWGLAIGHRRMRGT
53   ACIQSKQAFTFSPTYKAFLC   KQYLNLYPVARQRSGLCQVF   ADATPTGWGLVMGHQRMRGT
54   ACIQSKQAFTFSPTYKAFLC   KQYLNLYPVARQRPGLCQVF   ADATPTGWGLVMGHQRMRGT
55   ACIQSKQAFTFSPTYKAFLC   KQYLNLYPVAGQRPGLCQVF   ADATPTGWGLAMGHQRMRGT
56   ACIQSKQAFTFSPTYKAFLC   KQYLNLYPVARQRPGLCQVF   ADATPTGWGLGMGHQRMRGT
57   ACIQFKQAFTFSPTYKAFLC   KQYLNLYPVARQRPGLCQVF   ADATPTGWGLAIGNQRMRGT
58   ACIQAKQAFTFSPTYKAFLS   KQYLNLYPVARQRPGLCQVF   ADATPTGWGLAIGHQRMRGT
158  ACIQsKQAFTFSPTYKAFLc   kQYlnlyPVArQRpgLCQVF   ADATPTGWGLaiGhqrMRGt
```

FIG. 4M

```
      721
39    FVAPLPIHTAELLAACFARS    RSGAKLIGTDNSVVLSRKYT    SFPWLLGCAANWILRGTSFV
40    FVAPLPIHTAELLAACFARS    RSGAKLIGTDNSVVLSRKYT    SFPWLLGCAANWILRGTSFV
41    FVVPLPIHTAELLAACFARD    RSGAKLIGTDNSVVLSRKYT    SFPWLLGCAANWILRGTSFV
42    FVAPLPIHTAELLAACFARS    RSGAKLIGTDNSVVLSRKYT    SFPWLLGCAANWILRGTSFV
43    LWLLCRSILRNS
44    FVAPLPIHTAELLAACFARS    RSGAKLIGTDNSVVLSRKYT    SFPWLLGCAANWILRGTYFV
45    FVAPLPIHTAELLAACFARS    RSGAKLIGTDNSVVLSRKYT    SFPWLLGCAANWILRGTYFV
47    FVSPLPIHTAELLAACFARS    RSGAKLIGTDNSVVLSRKYT    SFPWLLGCAANWILRGTSFV
48    FVSPLPIHTAELLAACFARS    RSGANLIGTDNSVVLSRKYT    SFPWLLGCAANWILRGTSFV
49    FVSPLPIHTVELLAACFARS    RSGAKLIGTDNSVVLSRKYT    SFPWLLGCAANWILRGTSFV
50    FVSPLPIHTAELLAACFARS    RSGAKLIGTDNSVVLSRKYT    SFPWLLGCAANWILRGTSFV
51    FVAPLPIHTAELLAACFARS    RSGAKLIGTDNSVVLSRKYT    SFPWLLGCTANWILRGTSFV
52    FVAPLPIHTAELLAACFARS    RSGAKLIGTDNSVVLSRKYT    SFPWLLGCAANWILRGTSFV
53    FVAPLPIHTAELLAACFARS    RSGAKLIGTDNSVVLSRKYT    SFPWLLGCAANWILRGTSFV
54    FSAPLPIHTAELLAACFARS    RSGANIIGTDNSVVLSRKYT    SYPWLLGCAANWILRGTSFV
55    FLARLPIHTAELLAACFARS    RSGANILGTDNSVVLSRKYT    SFPWLLGCAANWILRGTSFV
56    FSAPLPIHTAELLAACFARS    RSGANLIGTDNSVVLSRKYT    SFPWLLGCAANWILRGTSFV
57    FSAPLPIHTAELLAACFARS    RSGANLIGTDNSVVLSRKYT    SFPWLLGCTANWILRGTSFV
58    IVAPLPIHTAELLAACFARS    RSGAKLIGTDNSVVLSRKYT    SfPWLLGCAANWILRGTSFV
158   fvaplpihtaellAACFARs    RSGAkliGTDNSVVLSRKYT    SfpWLLGCaANWILRGTsFV
```

FIG. 4N

```
    781
39  YVPSALNPADDPSRGRLGLY  RPLLLLPFRPTTGRTSLYAV  SPSVPSHLPDRVHFASPLHV
40  YVPSALNPADDPSRGRLGLY  RPLLHLPFRPTTGRTSLYAV  SPSVPSHLPDRVHFPSPLHV
41  YVPSALNPADDPSRGRLGLY  RPLLSLPFQPTTGRTSLYAV  SPSVPSHLPDRVHFASPLHV
42  YVPSALNPADDPSRGRLGLY  RPLLHLPFRPTTGRASLYAV  SPSVPSHLPVRVHFASPLHV
44  YVPSALNPADDPSRGRLGLI  RPLLHLRFRPTTGRTSLYAV  SPSVPSHLPDRVHFASPLHV
45  YVPSALNPADDPSRGRLGLI  RPLLHLRFRPTTGRTSLYAV  SPSVPSHLPDRVHFASPLHV
47  YVPSALNPADDPSRGRLGLY  RPLLRLPYRPTTGRTSLYAD  SPSVPSHLPDRVHFASPLHV
48  YVPSALNPADDPSRGRLGLY  RPLLRLLYRPTTGRTSLYAD  SPSVPSHLPDRVHFASPLHV
49  YVPSALNPADDPSRGRLGLY  RPLLRLPYRPTTGRTSLYAD  SPSVPSHLPDRVHFASPLHV
50  YVPSALNPADDPSRGRLGLY  RPLLRLPYRPTTGRTSLYAD  SPSVPSRLPDRVHFASPLHV
51  YVPSALNPADDPSRGRLGLS  RPLLRLPFQPTTGRTSLYAV  SPSVPSHLPVRVHFASPLHV
52  YVPSALNPADDPSRGRLGLS  RPLLRLPFQPTTGRTSLYAV  SPSVPSHLPVRVHFASPLHV
53  YVPSALNPADDPSRGRLGLY  RPLLHLPFRPTTGRTSLYAV  SPSVPSHLPDRVHFASPLHV
54  YVPSALNPADDPSRGRLGLS  RPLLRLPFRPTTGRTSLYAD  SPSVPSHLPDRVHFASPLHV
55  YVPSALNPADDPSRGRLGLS  RPLLRLPFRPTTGRTSLYAD  SPSVPSHLPDRVHFASPLHV
56  YVPSALNPADDPSRGRLGLS  RPLLRLPFRPTTGRTSLYAD  SPSVPSHLPDLVHFASPLHV
57  YVPSALNPADDPSRGRLGLS  RPLLCLPFRPTTGRTSLYAD  SPSVPSHLPDRVHFASPLHV
58  YVPSALNPADDPSRGRLGLS  RPLLRLPFQPTTGRTSLYAV  SPSVPSHLPVRVHFASPLHI
```

FIG. 40

| 841 | |
|---|---|
| 39 | AWRPP |
| 40 | AWRPP |
| 41 | AWRPP |
| 42 | AWRPP |
| 44 | AWRPP |
| 45 | AWRPP |
| 47 | AWRPP |
| 48 | AWRPP |
| 49 | AWRPP |
| 50 | AWRPP |
| 51 | AWRPP |
| 52 | AWRPP |
| 53 | AWRPP |
| 54 | AWRPP |
| 55 | AWRPP |
| 56 | AWRPP |
| 57 | AWRPP |
| 58 | AWRPP |
| 158 | AWRPP |

PEPTIDES FOR INDUCING CYTOTOXIC T LYMPHOCYTE RESPONSES TO HEPATITIS B VIRUS

RELATED APPLICATIONS

The present application is a continuation of application U.S. Ser. No. 100,870 filed Aug. 2, 1993, now abandoned, which is a continuation-in-part application of U.S. Ser. No. 07/935,898, filed Aug. 26, 1992, now abandoned, which is a continuation-in-part of U.S. Ser. No. 07/749,540, filed Aug. 26, 1991 (abandoned) the disclosures of which are incorporated herein by reference.

GOVERNMENT SUPPORT

The U.S. Government may have certain rights in this invention pursuant to grants awarded by the National Institutes of Health.

BACKGROUND OF THE INVENTION

Cytotoxic T lymphocytes (CTLs) play an essential role in fighting cells infected with viruses, intracellular bacteria and parasites, and tumor cells. They do so by direct cytotoxicity and by providing specific and nonspecific help to other immunocytes such as macrophages, B cells, and other T cells. Infected cells or tumor cells process antigen through intracellular events involving proteases. The processed antigen is presented on the cellular surface in the form of peptides bound to HLA class I molecules to T cell receptors on CTLs. MHC class I molecules can also bind exogenous peptides and present them to CTLs without intracellular processing.

At the present time it is difficult to accurately predict from the sequence of an antigenic protein how the protein will be processed and which peptide portions will bind HLA class I molecules and be presented to CTLs. Binding motifs have been predicted for some HLA class I molecules based on sequence analysis of peptides eluted from these molecules (Falk et al., *Nature* 351:290 (1991)). Further, of the peptides that are processed and do bind to HLA class I, which ones will contain CTL-recognizable epitopes is not yet predictable.

Hepatitis B Virus ("HBV") is a non-lytic virus which has currently infected approximately 250 million people worldwide. HBV infection in adults typically leads to an acute disease in the majority of cases, and to a chronic disease state in a minority of patients. This ratio of acute to chronic is reversed when the infection occurs close to the time of birth. There is an increased incidence of hepatocellular carcinoma in chronic HBV infection. A small percentage of individuals who are infected with HBV in adulthood develop fulminant hepatitis associated with a strong immune response with high lethality.

While there is no effective treatment for HBV infection, vaccines have been developed in recent years to prevent HBV infection. The vaccines employ either HBV surface antigen (HBsAg) purified from the plasma of chronic HBV carriers, or HBsAg produced by recombinant DNA technology. Synthetic HBsAg peptide-based vaccines have also been proposed. See, for example, U.S. Pat. Nos. 4,599,230 and 4,599,231. The anti-HBsAg vaccines, however, afford protection in only about 90% of immunized individuals. Those who are unimmunized, or immunized but unprotected, provide a significant reservoir of potential infection.

The contribution of CTLs to immunity to HBV antigens has been difficult to assess. Chisari et al. (*Microbial Pathogen.* 6:31 (1989)) have suggested that liver cell injury may be mediated by an HLA-Class I restricted. $CD8^+$ cytotoxic T cell response to HBV encoded antigens. Class I major histocompatibility (MHC) -restricted cytotoxic T lymphocyte responses have been identified for a variety of other viruses, such as influenza. For example, Townsend et al., *Cell* 44:959 (1986) reported that epitopes of an influenza virus nucleoprotein recognized by cytotoxic T lymphocytes could be defined by synthetic peptides. In attempting to define the cytotoxic T lymphocyte response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). Moriyama et al., *Science* 248:361–364 (1990), have reported that the HBV major envelope antigen is expressed at the hepatocyte surface in a form recognizable by envelope-specific antibodies and by MHC class I-restricted, $CD8^+$ cytotoxic T lymphocytes.

As there is a large reservoir of individuals chronically infected with HBV, it would be desirable to stimulate the immune response of these individuals to respond to appropriate HBV antigens and thereby eliminate their infection. It would also be desirable to prevent the evolution to a chronic HBV infection in individuals suffering from an acute phase infection. Further, as the presently approved HBV vaccines do not elicit protective immunity in about 10% of immunized individuals, it would be desirable to elicit more effective immunity, such as by increasing or diversifying the immunogenicity of the vaccines. Quite surprisingly, the present invention fulfills these and other related needs.

SUMMARY OF THE INVENTION

The present invention provides peptides which induce MHC class I restricted cytotoxic T lymphocyte responses against HBV antigen. The peptides of interest are derived from the sequence of the HBV polymerase protein. In certain embodiments the CTL inducing peptide will have the sequence of HBpol61–69 (Seq. ID No. 1), Gly-Leu-Tyr-Ser-Ser-Thr-Val-Pro-Val; HBpol 455–463 (SEQ ID NO 2); Gly-Leu-Ser-Arg-Tyr-Val-Ala-Arg-Leu; HBpol 773–782 (SEQ ID NO 3), Ile-Leu-Arg-Gly-Thr-Ser-Phe-Val-Tyr-Val; HBpol803–811 (Seq. ID No. 4), Ser-Leu-Tyr-Ala-Asp-Ser-Pro-Ser-Val; or HBpol816–824 (Seq. ID No. 5), Phe-Leu-Leu-Ser-Leu-Gly-Ile-His-Leu, or will have a sequence substantially homologous to one of the foregoing sequences. The peptide can be optionally flanked and/or modified at one or both of the N- and C-termini, as desired. Conservative substitutions, deletions and additions may be made at non-critical residue positions within the selected peptide without substantially adversely affecting its biological activity.

In the various peptide embodiments it will be understood that the peptides can be polymerized, each to itself to form larger homopolymers, or with different peptides to form heteropolymers. In some instances peptides will be combined in a composition as an admixture and will not be linked. The peptide can also be conjugated to a lipid-containing molecules capable of enhancing a T lymphocyte response, or to a different peptide which induces a T-helper cell response, for example.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective cytotoxic T cell responses against HBpol epitopes. For treating these infections it may be particularly desirable to combine the peptides which induce MHC class I restricted cytotoxic T lymphocyte responses against HBV antigen with other peptides or proteins that induce immune response to other HBV antigens, such as HBV envelope or core. To treat individuals with chronic or carrier state infections the compositions may be administered in repeated dosages over a prolonged period of time, as necessary, to resolve or substantially mitigate the infection and/or shedding of virus.

Vaccine compositions for preventing HBV infection, particularly chronic HBV infection, are also provided. The vaccine compositions comprise an immunogenically effective amount of a HBV polymerase peptide mentioned above which induces a MHC class I restricted cytotoxic T lymphocyte response, such as HLA-A2, and will typically further comprise an adjuvant, e.g., incomplete Freund's adjuvant or aluminum hydroxide. To achieve enhanced protection against HBV, the vaccine can further comprise components which elicit a protective antibody response to other HBV antigen, such as envelope (surface) antigen.

In yet other embodiments the invention relates to methods for diagnosis, where the peptides of the invention are used to determine the presence of lymphocytes in an individual which are capable of a cytotoxic T cell response to HBV polymerase antigen. The absence of such cells determines whether the individual of interest is susceptible to developing chronic HBV infection. Typically the lymphocytes are peripheral blood lymphocytes and the individual of interest is suffering from an acute HBV infection.

BRIEF DESCRIPTION OF THE DRAWINGS

FIG. 3 shows that the CTL response to polymerase peptide 803-811 can recognize cells pulsed with peptide and endogenously synthesized polymerase (Vpol), whereas the CTL response to polymerase peptide 61-69 only recognized cells pulsed with the 61-69 peptide.

FIGS. 4A-4O shows the aligned amino acid sequences of 20 cloned HBV polymerase proteins; line 158 is a consensus sequence where capital letters represent 100% consensus, lower case letters represent >50% consensus, and "." is <50% consensus.

DESCRIPTION OF THE SPECIFIC EMBODIMENTS

Figure 1:
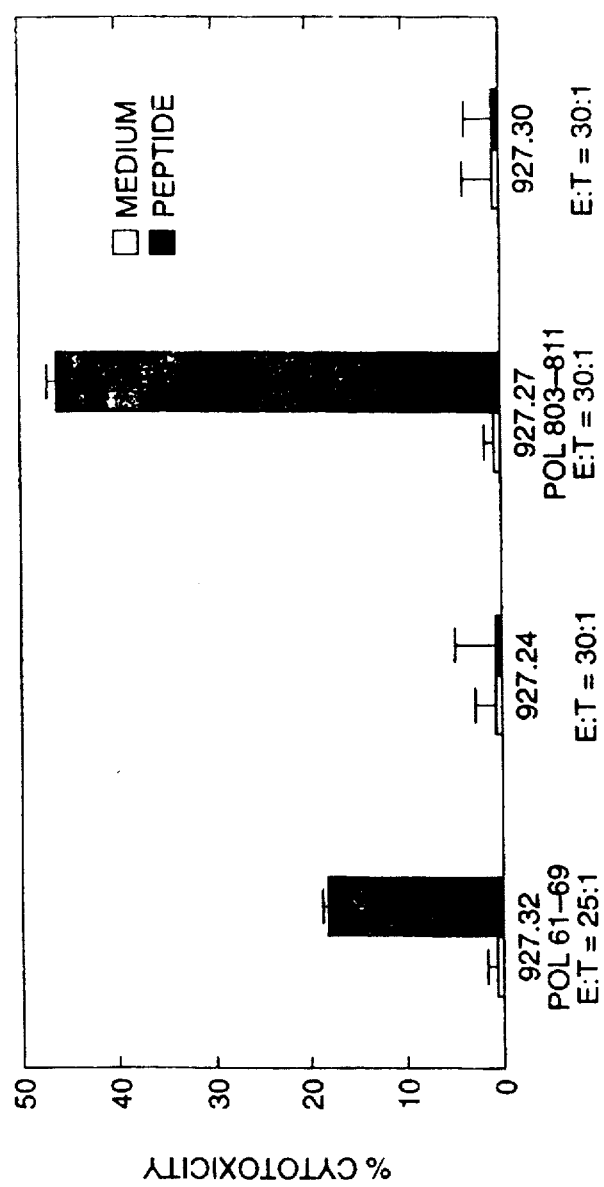
FIG. 1 shows the CTL response to two polymerase peptides that contain the HLA-A2 motif in a patient using target cells pulsed with peptide that match only at HLA-A2.

The present invention provides peptides derived from HBV polymerase proteins for use in compositions and methods for the treatment, prevention and diagnosis of HBV infection. The peptides stimulate MHC HLA-class I restricted cytotoxic T lymphocyte responses against HBV infected cells. The stimulated cytotoxic T lymphocytes are able to kill the infected cells or inhibit viral replication and thus interrupt or substantially prevent infection, including chronic HBV infection. A peptide effective in eliciting a cytotoxic T cell response may also be combined with an immunogen capable of eliciting a T-helper response.

The peptides employed in the invention are derived from the sequence of the HBV polymerase protein (HBpol), particularly CTL epitopes within $HBpol_{61-69}$, HBpol 455-463, HBpol 773-782, HBpol 803-811, and HBpol 816-824, where the numbering is according to Galibert et al., supra.

By HBV cytotoxic T lymphocyte inducing "peptide" or "oligopeptide" of the present invention is meant a chain of at least four HBV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues derived from an HBc sequence. It may be desirable to optimize peptides of the invention to a length of eight to twelve amino acid residues, commensurate in size with endogenously processed viral peptides that are bound to MHC class I molecules on the cell surface. See generally, Schumacher et al., Nature 350:703–706 (1991); Van Bleek et al., Nature 348:213–216 (1990); Rotzschke et al., Nature 348:252–254 (1990); and Falk et al., Nature 351:290–296 (1991), which are incorporated herein by reference. As set forth in more detail below, usually the peptides will have at least a majority of amino acids which are homologous to a corresponding portion of contiguous residues of the HBV pol sequences herein, and contain a CTL-inducing epitope.

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. By biological activity is meant the ability to bind an appropriate MHC molecule and induce a cytotoxic T lymphocyte response against HBV antigen or antigen mimetic. By a cytotoxic T lymphocyte response is meant a $CD8^+$ T lymphocyte response specific for an HBV antigen of interest, wherein $CD8^+$, MHC class I-restricted T lymphocytes are activated. The activated T lymphocytes secrete lymphokines (e.g., gamma interferon) liberate products (e.g., serine esterases) that inhibit viral replication in infected autologous cells or transfected cells, with or without cell killing.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

The peptides of the invention contain CTL-inducing epitopes derived from various epitopic regions of the HBV polymerase protein. The peptides are from the region of HBpol$_{61-69}$ and include peptides derived from those sequence regions which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBpol$_{61-69}$ sequence, where HBpol$_{61-69}$ has the following sequence (for HBV subtype ayw):

(HBpol$_{61-69}$) [Seq. ID No. 1]

Gly-Leu-Tyr-Ser-Ser-Thr-Val-Pro-Val, and

The peptide embodiments of this HBpol$_{61-69}$ region and the other polymerase peptide regions described herein can be optionally flanked and/or modified at one or both of the N- and C-termini, as desired, by amino acids from HBV sequences, including HBpol, amino acids added to facilitate linking, other N- and C-terminal modifications, linked to carriers, etc., as further described herein. The peptide HBpol61–69 induces a cytotoxic T lymphocyte response which is mediated by at least the MHC class I molecule HLA-A2.

Other HBpol region peptides containing CTL epitopes of the invention comprises the peptide HBpol 455–463, and peptides derived from HBpol455–463 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol455–463 sequence, where HBpol 455–463 has the sequence (for HBV subtype ayw):

(HBpol 455–463) [SEQ ID NO 2]

Gly-Leu-Ser-Arg-Tyr-Val-Ala-Arg-Leu wherein the selected peptide can be flanked and/or modified at one or both termini as described herein. The peptide HBpol 455–463 induces a cytotoxic T lymphocyte response which is mediated by at least the MHC class I molecule HLA-A2. Other HBpol region peptides containing CTL epitopes of the invention comprises the peptide HBpol 773–782, and peptides derived from HBpol773–782 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBpol773–782 sequence, where HBpol 773–782 has the sequence (for HBV subtype ayw):

(HBpol 773–782) [SEQ ID NO 3]

Ile-Leu-Arg-Gly-Thr-Ser-Phe-Val-Tyr-Val wherein the selected peptide can be flanked and/or modified at one or both termini as described herein. The peptide HBpol 773–782 induces a cytotoxic T lymphocyte response which is mediated by at least the MHC class I molecule HLA-A2. Other HBpol peptide embodiments of the invention are prepared from the region of HBpol803–811. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol803–811 sequence, where HBpol803–811 has the sequence (for HBV subtype ayw):

(HBpol$_{803-811}$) [Seq. ID No. 4]

Ser-Leu-Tyr-Ala-Asp-Ser-Pro-Ser-Val, wherein the selected peptide can be flanked and/or modified at one or both termini as described herein. The peptide HBpol 803–811 induces a cytotoxic T lymphocyte response which is mediated by at least the MHC class I molecule HLA-A2.

Other HBpol peptide embodiments of the invention are prepared from the region of HBpol816–824. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBpol816–824 sequence, where HBpol816–824 has the sequence (for HBV subtype ayw):

(HBpol$_{816-824}$) [Seq. ID No. 5]

Phe-Leu-Leu-Ser-Leu-Gly-Ile-His-Leu, wherein the selected peptide can be flanked and/or modified at one or both termini as described herein. The peptide HBpol 816–824 induces a cytotoxic T lymphocyte response which is mediated by at least the MHC class I molecule HLA-A2.

As mentioned above, additional amino acids can be added to the termini of an oligopeptide or peptide to provide for ease of linking peptides one to another, for coupling to a carrier, support or a larger peptide, for reasons discussed herein, or for modifying the physical or chemical properties of the peptide or oligopeptide, and the like. Amino acids such as tyrosine, cysteine, lysine, glutamic or aspartic acid, and the like, can be introduced at the C- or N-terminus of the peptide or oligopeptide. In addition, the peptide or oligopeptide sequences can differ from the natural sequence by being modified by terminal-NH$_2$ acylation, e.g., acetylation, or thioglycolic acid amidation, terminal-carboxy amidation, e.g., ammonia, methylamine, etc. In some instances these modifications may provide sites for linking to a support or other molecule.

It will be understood that the HBV peptides of the present invention or analogs or homologs thereof which have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, e.g., the addition or deletion of amino acids on either the amino terminal or carboxy terminal end, or both, of peptides derived from the sequences disclosed herein. The peptides may be modified to substantially enhance the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

The peptides employed in the subject invention need not be identical to peptides HBpol61–69 (Seq. ID No. 1), Gly-Leu-Tyr-Ser-Ser-Thr-Val-Pro-Val; HBpol 455–463 (SEQ ID NO 2); Gly-Leu-Ser-Arg-T yr-Val-Ala-Arg-Leu; HBpol 773–782 (SEQ ID NO 3), Ile-Leu-Arg-Gly-Thr-Ser-Phe-Val-Tyr-Val; HBpol803–811 (Seq. ID No. 4), Ser-Leu-Tyr-Ala-Asp-Ser-Pro-Ser-Val; or HBpol816–824 (Seq. ID No. 5), Phe-Leu-Leu-Ser-Leu-Gly-Ile-His-Leu, so long as the subject compounds are able to provide for cytotoxic T lymphocytic activity against at least one of the four major subtypes of HBV. Although different strains of HBV exist, they each share at least one common envelope determinant, which is designated "a". Each strain also has two other envelope determinants, one of which is either "d" or "y", and the second is either "w" or "r". Thus, there are four possible subtypes of the virus: adw, ayw, adr, and ayr. The cloning, sequencing and expression of HBV are described in GB 2034323, EP 13828, U.S. Pat. No. 4,935,235, and the complete sequence of the HBV envelope region is also described in Galibert et al., *Nature* 281:646 (1979), each of the foregoing being incorporated herein by reference. Amino acid sequences are described in the GenBank-72 database for 20 different HBV strains, including 7 of the adw subtype, 5 of the ayw subtype, 7 of the adr subtype, and 1 strain of the ayr subtype, the GenBank sequences also being incorporated herein by reference.

Therefore, the peptides may be subject to various changes, such as insertions, deletions, and substitutions, either conservative or non-conservative, where such changes provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV cytotoxic T lymphocyte stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. Where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequences identified by the present invention, including the representative peptides listed above, there are residues (or those which are substantially functionally equivalent) which allow the peptide to retain their biological activity, i.e., the ability to stimulate a class I-restricted cytotoxic T-lymphocytic response against HBV infected cells or cells which express HBV antigen. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid steric and charge interference which might disrupt binding.

Peptides which tolerate multiple substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the invention provides methods for identifying other epitopic regions associated with said peptide regions capable of inducing MHC-restricted cytotoxic T lymphocyte responses against HBV. The methods comprise obtaining peripheral blood lymphocytes (PBL) from infected or uninfected individuals and exposing (stimulating) the cells with synthetic peptide or polypeptide fragments derived from a peptide region of HBpol61–69 (Seq. ID No. 1), Gly-Leu-Tyr-Ser-Ser-Thr-Val-Pro-Val; HBpol 455–463 (SEQ ID NO 2); Gly-Leu-Ser-Arg-Tyr-Val-Ala-Arg-Leu; HBpol 773–782 (SEQ ID NO 3), Ile-Leu-Arg-Gly-Thr-Ser-Phe-Val-Tyr-Val; HBpol803–811 (Seq. ID No. 4), Ser-Leu-Tyr-Ala-Asp-Ser-Pro-Ser-Val; or HBpol816–824 (Seq. ID No. 5), Phe-Leu-Leu-Ser-Leu-Gly-Ile-His-Leu. Pools of overlapping synthetic peptides, each typically about 8 to 20 residues long, preferably 9–12 residues, can be used to stimulate the cells. Active peptides can be selected from pools which induce cytotoxic T lymphocyte activity. The ability of the peptides to induce specific cytotoxic activity is determined by incubating the stimulated PBL with autologous labeled (e.g., $^{51}Cr$) target cells (such as HLA matched macrophages, T cells, fibroblasts or B lymphoblastoid cells) infected or transfected with the HBV subgenomic fragments thereof, such that the targeted antigen is synthesized endogenously by the cell (or the cell is pulsed with the peptide of interest), and measuring specific release of label.

Once a peptide having an epitopic region which stimulates a cytotoxic T lymphocyte response is identified, the MHC restriction element of the response can be determined. This involves incubating the stimulated PBL or short term lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Carbone et al., *J. Exp. Med.* 167:1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HBV proteins would be undesirable in the development of HBV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HBV antigen, e.g., HBpol. Cells having activity are also stimulated with an appropriate T cell mitogen, e.g., phytohemagglutinin (PHA). The restimulated cells are provided with irradiated allogeneic PBLs as an antigen nonspecific source of T cell help, and HBV antigen. To selectively expand the population of cytotoxic T lymphocytes that recognize native HBV antigen and to establish long term lines, PBL from a patient are first stimulated with peptide and recombinant or native HBV antigen, followed by restimulation with HLA-matched B lymphoblastoid cells that stably express the corresponding HBV antigen polypeptide. The cell lines are re-confirmed for the ability to recognize endogenously synthesized antigen using autologous and allogeneic B-lymphoblastoid or other cells transfected or infected with appropriate antigen.

Having identified different peptides of the invention which contribute to inducing anti-HBV cytotoxic T lymphocyte responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g., the HBpol61–69 (Seq. ID No. 1), Gly-Leu-Tyr-Ser-Ser-Thr-Val-Pro-Val; HBpol 455–463 (SEQ ID NO 2), Gly-Leu-Ser-Arg-Tyr-Val-Ala-Arg-Leu; HBpol 773–782 (SEQ ID NO 3), Ile-Leu-Arg-Gly-Thr-Ser-Phe-Val-Tyr-Val; HBpol803–811 (Seq. ID No. 4), Ser-Leu-Tyr-Ala-Asp-Ser-Pro-Ser-Val; or HBpol816–824 (Seq. ID No. 5), Phe-Leu-Leu-Ser-Leu-Gly-Ile-His-Leu peptides, which peptides can be combined in a "cocktail" to provide enhanced immunogenicity for cytotoxic T lymphocyte responses. Moreover, peptides of one region can be combined with peptides of other HBV regions, from the same or different HBV protein, particularly when a second or subsequent peptide has a MHC restriction element different from the first. Other CTL-inducing HBV peptides are described in co-pending application U.S. Ser. Nos. 07/935,898 and 08/024,120, which are incorporated herein by reference. This composition of peptides can be used to effectively broaden the immunological coverage provided by therapeutic, vaccine or diagnostic methods and compositions of the invention among a diverse population. For example, the different frequencies of HLA alleles among prevalent ethnic groups (caucasian, asian and african blacks) are shown in Table I below. Therapeutic or vaccine compositions of the invention may be formulated to provide potential therapy or immunity to as high a percentage of a population as possible.

TABLE I

HLA ALLELE FREQUENCIES AMONG PREVALENT ETHNIC GROUPS

| HLA Allele | EUC | NAC | AFR | JPN |
|---|---|---|---|---|
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 7.7 | 9.9 | 16.6 | 1.1 |

Abbreviations: EUC, European Caucasian; NAC, North American Caucasian; AFR, African blacks; JPN, Japanese.
*A28 represents the two alleles Aw68 and Aw69

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, a peptide which contains T helper epitopes, heteropolymers with repeating units are provided. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyl-dithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane- 1-carboxylic acid and the like. The carboxyl groups can be activated by combining them with succinimide or 1-hydroxy-2-nitro-4- sulfonic acid, sodium salt. A particularly preferred coupling agent is succinimidyl 4-(N-maleimidomethyl) cyclohexane- 1-carboxylate (SMCC). It will be understood that linkage should not substantially interfere with either of the linked groups to function as described, e.g., as an HBV cytotoxic T cell determinant, peptide analogs, or T helper determinant.

In another aspect the peptides of the invention can be combined or coupled with other peptides which present HBV T-helper cell epitopes, i.e., epitopes which stimulate T cells that cooperate in the induction of cytotoxic T cells to HBV. The T-helper cells can be either the T-helper 1 or T-helper 2 phenotype, for example. T-helper epitopes from HBV sequences have been identified at HBcl-20, having the sequence: Met-Asp-Ile-Asp-Pro-Tyr-Lys-Glu-Phe-Gly-Ala-Thr-Val-Glu-Leu-Leu-Ser-Phe-Leu-Pro (Seq. ID No. 6). Other T-helper epitopes are provided by peptides from the region HBc50 . 69, having the sequence Pro-His-His-Tyr-Ala-Leu-Arg-Gln-Ala-Ile-Leu-Cys-Trp-Gly-Glu-Leu-Met- Tyr-Leu-Ala (Seq. ID No. 7), and from the region of HBc100–139, including HBc100–119 having the sequence Leu-Leu-Trp-Phe-His-Ile-Ser-Cys-Leu-Thr-Phe-Gly-Arg-Glu-Thr-Val-Ile-Glu-Tyr-Leu (Seq. ID No. 8) (where Ile$_{116}$ is Leu in the HBV adw subtype), HBc117–131 having the sequence Glu-Tyr-Leu-Val-Ser-Phe-Gly-Val-Trp-Ile-Arg-Thr-Pro-Pro-Ala (Seq. ID No. 9), and peptide HBc120–139 having the sequence Val-Ser-Phe-Gly-Val-Trp-Ile-Arg-Thr-Pro-Pro-Ala-Tyr-Arg-Pro-Pro-Asn-Ala-Pro-Ile (Seq. ID No. 10). See, Ferrari et al., *J. Clin. Invest.* 88:214–222 (1991), and U.S. Pat. No. 4,882,145, each incorporated herein by reference.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), and Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, whose disclosures are each incorporated herein by reference. Thus, fusion proteins which comprise one or more peptide sequences of the invention can be used to present the HBV cytotoxic T cell determinants. For example, a recombinant polymerase protein of the invention is prepared in which the HBpol amino acid sequence is altered so as to more effectively present epitopes of peptide regions described herein to stimulate a cytotoxic T lymphocyte response. By this means a polypeptide is used which incorporates several T cell epitopes.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range from about 1 μg to about 2,000 mg of peptide for a 70 kg patient, with dosages of from about 10 μg to about 100 mg of peptide being more commonly used, followed by booster dosages from about 1 μg to about 1 mg of peptide over weeks to months, depending on a patient's CTL response, as determined by measuring HBV-specific CTL activity in PBLs obtained from the patient. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals, about 90% of whom are capable of resolving the infection naturally. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3–6 months after infection. As individuals may develop chronic HBV infection because of an inadequate (or absent) cytotoxic T lymphocyte response during the acute phase of their infection, it is important to provide an amount of immunopotentiating peptide in a formulation and mode of administration sufficient to effectively stimulate a cytotoxic T cell response. Thus, for treatment of chronic hepatitis, a representative dose is in the range of about 1 µg to 1,000 mg, preferably about 5 µg to 100 mg for a 70 kg patient per dose. Administration should continue until at least clinical symptoms or laboratory indicators indicate that the HBV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the cytotoxic T-lymphocyte stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified which are capable of priming CTL in vivo against viral antigens, e.g., tripalmitoyl-S-glycerylcysteinly-seryl-serine ($P_3CSS$), which can effectively prime virus specific cytotoxic T lymphocytes when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a cytotoxic T lymphocyte response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection.

The concentration of cytotoxic T-lymphocyte stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Science*, 17th ed., Mack Publishing Company, Easton, Pa. (1985), which is incorporated herein by reference.

The peptides of the invention may also be administered via liposomes, which serve to target the peptides to a particular tissue, such as lymphoid tissue or HBV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, the mode of administration, the peptide being delivered, the stage of disease being treated, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the cytotoxic T-lymphocyte stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included as desired, e.g., lecithin for intranasal delivery.

In another aspect the present invention is directed to vaccines which contain as an active ingredient an immunogenically effective amount of a cytotoxic T-lymphocyte stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., keyhole limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HBV antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 µg to about 500 mg per 70 kilogram patient, more commonly from about 50 µg to about 200 mg per 70 kg of body weight. The peptides are administered to individuals of an appropriate HLA type, e.g., for vaccine compositions of peptides from the region of HBpol61–69 (Seq. ID No. 1), Gly-Leu-Tyr-Ser-Ser-Thr-Val-Pro-Val; HBpol 455–463 (SEQ ID NO 2); Gly-Leu-Ser-Arg-Tyr-Val-Ala-Arg-Leu; HBpol 773–782 (SEQ ID NO 3), Ile-Leu-Arg-Gly-Thr-Ser-Phe-Val-Tyr-Val; HBpol803–811 (Seq. ID No. 4), Ser-Leu-Tyr-Ala-Asp-Ser-Pro-Ser-Val; or HBpol816–824 (Seq. ID No. 5), Phe-Leu-Leu-Ser-Leu-Gly-Ile-His-Leu, these will be administered to at least HLA-A2 individuals.

In some instances it may be desirable to combine the peptide vaccines of the invention with vaccines which induce neutralizing antibody responses to HBV, particularly to HBV envelope and/or core antigens, such as recombinant HBV env- and/or nucleocapside-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, EP 154,902 and EP 291, 586, and U.S. Pat. Nos. 4,565,697, 4,624,918, 4,599,230, 4,599,231, 4,803,164, 4,882,145, 4,977,092, 5,017,558 and 5,019,386, each being incorporated herein by reference. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HBV peptides of the invention. Upon introduction into an acutely or chronically HBV-infected host or into a non-infected host, the recombinant vaccinia virus expresses the HBV peptide and thereby elicits a host cytotoxic T lymphocyte response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy. By ex vivo therapy is meant that therapeutic or immunogenic manipulations are performed outside the body. For example, lymphocytes or other target cells may be removed from a patient and treated with high doses of the subject peptides, providing a stimulatory concentration of peptide in the cell medium far in excess of levels which could be accomplished or tolerated by the patient. Following treatment to stimulate the CTLs, the cells are returned to the host to treat the HBV infection. The host's cells may also be exposed to vectors which carry genes encoding the peptides, as described above. Once transfected with the vectors, the cells may be propagated in vitro or returned to the patient. The cells which are propagated in vitro may be returned to the patient after reaching a predetermined cell density.

In one method, ex vivo CTL responses to a HBV are induced by incubating in tissue culture a patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (an HBV infected cell). To optimize the in vitro conditions for the generation of specific cytotoxic T cells, the culture of stimulator cells is typically maintained in an appropriate serum-free medium. Peripheral blood lymphocytes are conveniently isolated following simple venipuncture or leukapheresis of normal donors or patients and used as the responder cell sources of CTLp. In one embodiment, the appropriate APC are incubated with about 10–100 µM of peptide in serum-free media for 4 hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of the HBV polymerase antigen from which the peptide sequence was derived. Specificity and MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides.

The induction of CTL in vitro requires the specific recognition of peptides that are bound to allele specific MHC class I molecules on APC. Peptide loading of empty major histocompatibility complex molecules on cells allows the induction of primary CTL responses. Since mutant cell lines do not exist for every human MHC allele, it may be advantageous to use a technique to remove endogenous MHC-associated peptides from the surface of APC, followed by loading the resulting empty MHC molecules with the immunogenic peptides of interest. The use of non-transformed, non-infected cells, and preferably, autologous cells of patients as APC is desirable for the design of CTL induction protocols directed towards development of ex vivo CTL therapies. Typically, prior to incubation of the APCs with the CTLp to be activated, an amount of antigenic peptide is added to the APC or stimulator cell culture, of sufficient quantity to become loaded onto the human Class I molecules to be expressed on the surface of the APCs. Resting or precursor CTLs are then incubated in culture with the appropriate APCs for a time period sufficient to activate the CTLs. Preferably, the CTLs are activated in an antigen-specific manner. The ratio of resting or precursor CTLs to APCs may vary from individual to individual and may further depend upon variables such as the amenability of an individual's lymphocytes to culturing conditions and the nature and severity of the disease condition or other condition for which the described treatment modality is used. Preferably, however, the CTL:APC ratio is in the range of about 30:1 to 300:1. The CTL/APC may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged molecules may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$–$5 \times 10^7$ cells used in mice.

Methods of reintroducing cellular components are known in the art and include procedures such as those exemplified in U.S. Pat. No. 4,844,893 to Honsik, et al. and U.S. Pat. No. 4,690,915 to Rosenberg, which are incorporated herein by reference. For example, administration of activated CTLs via intravenous infusion is typically appropriate.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE I

HLA-Restricted CTL Response TO HBV Polymerase Epitopes

This Example describes the identification of an HLA-A2 restricted CTL response to two HBV polymerase peptides in a patient with acute viral hepatitis. The epitopes are present in amino acid sequences HBpol$_{61-69}$ [Seq. ID No. 1] Gly-Leu-Tyr-Ser-Ser-Thr-Val-Pro-Val (GLYSSTVPV) (also designated peptide 927.32) and HBpol$_{803-811}$ [Seq. ID No. 4] Ser-Leu-Tyr-Ala-Asp-Ser-Pro-Ser-Val (SLYADSPSV) (also designated peptide 927.27).

The CTL induced by the HBpol peptides were identified in PBMCs from a patient with acute hepatitis according to the procedure set forth in Example VI of pending application U.S. Ser. No. 07/935,898, except that the PMBCs were stimulated with individual peptides rather than peptide mixtures. The resulting CTL lines and/or clones were then tested for the ability to kill HLA-A2 matched target cells that were either pulsed with the peptide or that expressed the corresponding endogenous polymerase antigen (Vpol or EBO-pol).

Construction of the vaccinia based Vpol and Epstein-Barr virus based EBO-pol constructs was as described in Example II of U.S. Ser. No. 07/935,898

Figure 2:
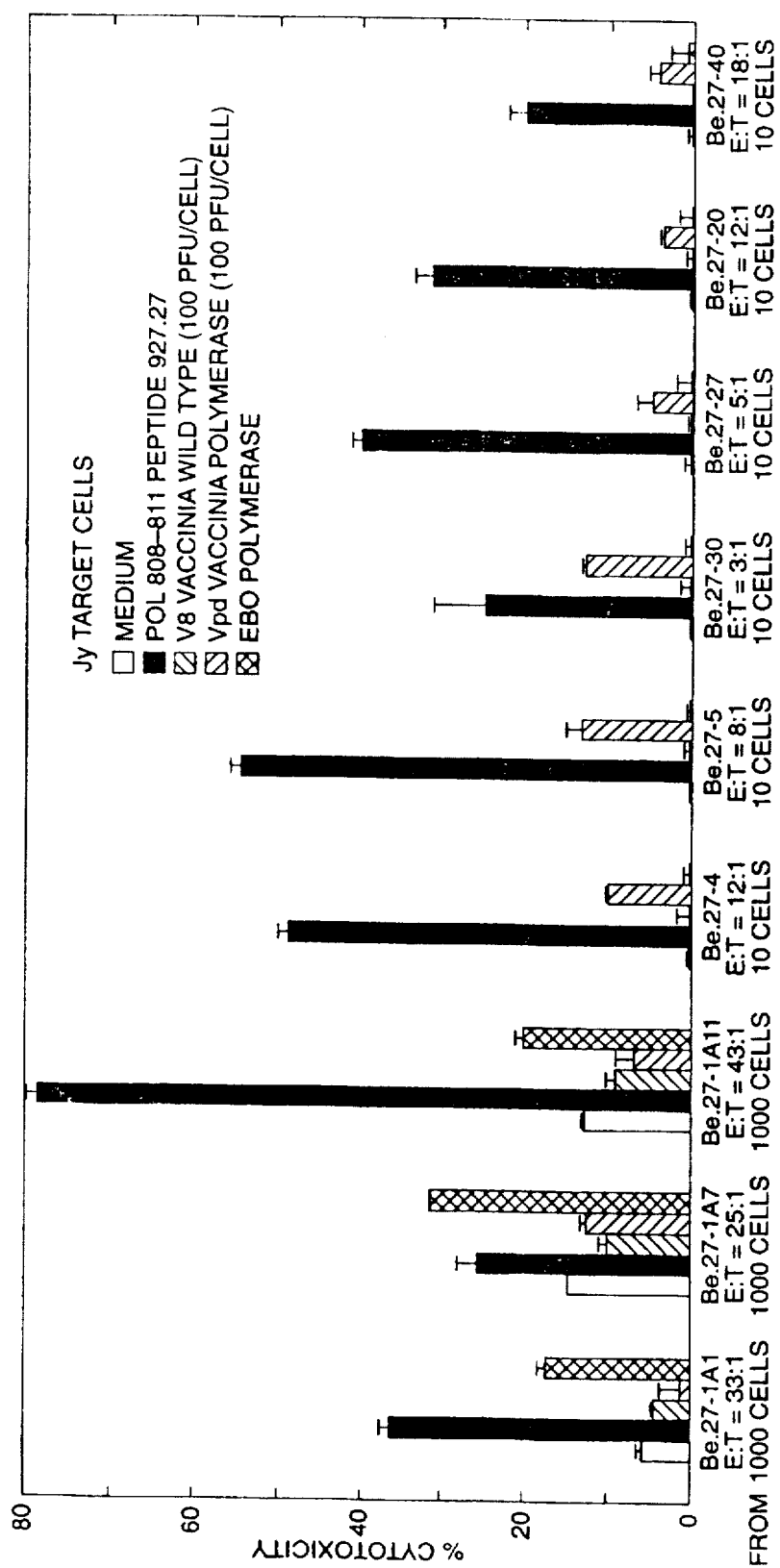
FIG. 2 shows the ability of several polymerase 803-811 peptide specific clones to recognize endogenously synthesized polymerase.

As shown in FIG. 1, both peptides HBpol$_{803-811}$ and HBpol$_{61-69}$ stimulated CTL responses in a patient (HLA-A2+) using target cells pulsed with peptide, whereas other peptides 927.24 (WILRGTSFR) and 927.30 (DLNLGNLNV) and media controls did not stimulate the specific CTL response. The ability of the HBpol$_{803-811}$ specific clones to recognize endogenously synthesized polymerase antigen (Vpol and EBO-pol) is shown in FIG. 2. Two clones, designated Be.27-1A1 and Be.27-1A5, were identified that recognized the HBpol$_{803-811}$ peptide. As shown in FIG. 3, CTL responses to HBpol$_{61-69}$ and HBpol$_{803-811}$ were shown with target cells pulsed with homologous peptide, but only the HBpol$_{803-811}$ clone showed a response to endogenously synthesized Vpol antigen.

All publications, patents and patent applications mentioned in this specification are herein incorporated by reference into the specification to the same extent as if each individual publication, patent or patent application was specifically and individually indicated to be incorporated herein by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A peptide containing at least one cytotoxic T lymphocyte (CTL) epitope, the peptide comprising no more than thirteen and at least eight amino acids wherein the peptide includes at least seven contiguous amino acids from a corresponding portion of HBpol having the sequence:

(HBpol 455-463)　　　　　　　　　　　(SEQ ID NO:2)

Gly-Leu-Ser-Arg-Tyr-Val-Ala-Arg-Leu.

2. The peptide of claim 1, which comprises from nine to eleven amino acids.

3. The peptide of claim 1, which comprises:

(HBpol 455-463)　　　　　　　　　　　(SEQ ID NO 2)

Gly-Leu-Ser-Arg-Tyr-Val-Ala-Arg-Leu.

4. An immunogenic composition comprising the peptide of claim 1 suspended in a pharmaceutically acceptable carrier which comprises a liposome.

5. An immunogenic composition comprising the peptide of claim 1 and a T helper epitope.

6. An immunogenic conjugate composition comprising the peptide of claim 1, conjugated to a immunogenic lipid carrier.

7. The immunogenic composition of claim 5, wherein the peptide is conjugated to the T helper epitope.

* * * * *

UNITED STATES PATENT AND TRADEMARK OFFICE
CERTIFICATE OF CORRECTION

| | | |
|---|---|---|
| PATENT NO. | : 5,780,036 | Page 1 of 1 |
| APPLICATION NO. | : 08/416950 | |
| DATED | : July 14, 1998 | |
| INVENTOR(S) | : Francis V. Chisari | |

It is certified that error appears in the above-identified patent and that said Letters Patent is hereby corrected as shown below:

Column 1,
Line 15, "The U.S. Government may have certain rights in this invention pursuant to grants awarded by the National Institutes of Health." Should read --A portion of the work described herein was supported by grant number AI20001 from the National Institutes of Health. The United States Government has certain rights in this invention.--

Signed and Sealed this

Fifth Day of February, 2008

JON W. DUDAS
*Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Leu  Tyr  Ser  Ser  Thr  Val  Pro  Val
1                      5
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Gly  Leu  Ser  Arg  Tyr  Val  Ala  Arg  Leu
1                      5
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ile  Leu  Arg  Gly  Thr  Ser  Phe  Val  Tyr  Val
1                      5                      10
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser  Leu  Tyr  Ala  Asp  Ser  Pro  Ser  Val
1                      5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Phe Leu Leu Ser Leu Gly Ile His Leu
1               5
```

( 2 ) INFORMATION FOR SEQ ID NO:6:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:6:

```
Met Asp Ile Asp Pro Tyr Lys Glu Phe Gly Ala Thr Val Glu Leu Leu
1               5                   10                  15
Ser Phe Leu Pro
            20
```

( 2 ) INFORMATION FOR SEQ ID NO:7:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:7:

```
Pro His His Tyr Ala Leu Arg Gln Ala Ile Leu Cys Trp Gly Glu Leu
1               5                   10                  15
Met Tyr Leu Ala
            20
```

( 2 ) INFORMATION FOR SEQ ID NO:8:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:8:

```
Leu Leu Trp Phe His Ile Ser Cys Leu Thr Phe Gly Arg Glu Thr Val
1               5                   10                  15
Ile Glu Tyr Leu
            20
```

( 2 ) INFORMATION FOR SEQ ID NO:9:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:9:

```
Glu Tyr Leu Val Ser Phe Gly Val Trp Ile Arg Thr Pro Pro Ala
1               5                   10                  15
```

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Val  Ser  Phe  Gly  Val  Trp  Ile  Arg  Thr  Pro  Pro  Ala  Tyr  Arg  Pro  Pro
 1              5                        10                       15

Asn  Ala  Pro  Ile
              20
```

( 2 ) INFORMATION FOR SEQ ID NO:11:

( i ) SEQUENCE CHARACTERISTICS:
        ( A ) LENGTH: 845 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Met  Pro  Leu  Ser  Tyr  Gln  His  Phe  Arg  Lys  Leu  Leu  Leu  Leu  Asp  Asp
 1              5                        10                       15

Gly  Thr  Glu  Ala  Gly  Pro  Leu  Glu  Glu  Leu  Pro  Arg  Leu  Ala  Asp
              20                        25                       30

Glu  Gly  Leu  Asn  Arg  Arg  Val  Ala  Glu  Asp  Leu  Asn  Gly  Asn  Leu
              35                        40                       45

Asn  Val  Ser  Ile  Pro  Trp  Thr  His  Lys  Val  Gly  Asn  Phe  Thr  Gly  Leu
 50                       55                        60

Tyr  Ser  Ser  Thr  Val  Pro  Val  Phe  Asn  Pro  Glu  Trp  Gln  Thr  Pro  Ser
 65                       70                        75                       80

Phe  Pro  Asn  Ile  His  Leu  Gln  Glu  Asp  Ile  Ile  Asn  Arg  Cys  Gln  Gln
                         85                        90                       95

Phe  Val  Gly  Pro  Leu  Thr  Val  Asn  Glu  Lys  Arg  Arg  Leu  Lys  Leu  Ile
              100                       105                      110

Met  Pro  Ala  Arg  Phe  Tyr  Pro  Asn  Val  Thr  Lys  Tyr  Leu  Pro  Leu  Asp
              115                       120                      125

Lys  Gly  Ile  Lys  Pro  Tyr  Tyr  Pro  Glu  His  Leu  Val  Asn  His  Tyr  Phe
      130                       135                      140

Gln  Thr  Arg  His  Tyr  Leu  His  Thr  Leu  Trp  Lys  Ala  Gly  Ile  Leu  Tyr
145                       150                      155                      160

Lys  Arg  Glu  Thr  Thr  Arg  Ser  Ala  Ser  Phe  Cys  Gly  Ser  Pro  Tyr  Ser
                         165                       170                      175

Trp  Glu  Gln  Glu  Leu  Gln  His  Gly  Arg  Leu  Val  Phe  Gln  Thr  Ser  Thr
              180                       185                      190

Arg  His  Gly  Asp  Glu  Ser  Phe  Cys  Ser  Gln  Ser  Ser  Gly  Ile  Leu  Ser
      195                       200                      205

Arg  Ser  Pro  Val  Gly  Pro  Cys  Ile  Arg  Ser  Gln  Leu  Arg  Gln  Ser  Arg
      210                       215                      220

Leu  Gly  Leu  Gln  Pro  Gln  Gln  Gly  His  Leu  Ala  Arg  Arg  Gln  Gln  Gly
225                       230                      235                      240

Arg  Ser  Gly  Ser  Ile  Arg  Ala  Arg  Val  His  Pro  Thr  Thr  Arg  Arg  Ser
                         245                       250                      255
```

-continued

| | | | | | | | | | | | | | | | |
|---|---|---|---|---|---|---|---|---|---|---|---|---|---|---|---|
| Phe | Gly | Val | Glu 260 | Pro | Ser | Gly | Ser | Gly 265 | His | Ile | Asp | Asn | Ser 270 | Ala | Ser |
| Ser | Ser | Ser 275 | Ser | Cys | Leu | His | Gln 280 | Ser | Ala | Val | Arg | Lys 285 | Ala | Ala | Tyr |
| Ser | His 290 | Leu | Ser | Thr | Ser | Lys 295 | Arg | Gln | Ser | Ser | Ser 300 | Gly | His | Ala | Val |
| Glu 305 | Leu | His | Asn | Ile | Pro 310 | Pro | Asn | Ser | Ala | Arg 315 | Ser | Gln | Ser | Glu | Gly 320 |
| Pro | Val | Phe | Ser | Cys 325 | Trp | Trp | Leu | Gln | Phe 330 | Arg | Asn | Ser | Lys 335 | Pro | Cys |
| Ser | Asp | Tyr | Cys 340 | Leu | Thr | His | Ile | Val 345 | Asn | Leu | Leu | Glu | Asp 350 | Trp | Gly |
| Pro | Cys | Thr 355 | Glu | His | Gly | Glu | His 360 | Asn | Ile | Arg | Ile | Pro 365 | Arg | Thr | Pro |
| Ala | Arg 370 | Val | Thr | Gly | Gly | Val 375 | Phe | Leu | Val | Asp | Lys 380 | Asn | Pro | His | Asn |
| Thr 385 | Thr | Glu | Ser | Arg | Leu 390 | Val | Val | Asp | Phe | Ser 395 | Gln | Phe | Ser | Arg | Gly 400 |
| Ser | Thr | Arg | Val | Ser 405 | Trp | Pro | Lys | Phe | Ala 410 | Val | Pro | Asn | Leu | Gln 415 | Ser |
| Leu | Thr | Asn | Leu 420 | Leu | Ser | Ser | Asn | Leu 425 | Ser | Trp | Leu | Ser | Leu 430 | Asp | Val |
| Ser | Ala | Ala 435 | Phe | Tyr | His | Ile | Pro 440 | Leu | His | Pro | Ala | Ala 445 | Met | Pro | His |
| Leu | Leu 450 | Val | Gly | Ser | Ser | Gly 455 | Leu | Ser | Arg | Tyr | Val 460 | Ala | Arg | Leu | Ser |
| Ser 465 | Asn | Ser | Arg | Ile | Ile 470 | Asn | Tyr | Gln | His | Gly 475 | Thr | Met | Gln | Asn | Leu 480 |
| His | Asp | Ser | Cys | Ser 485 | Arg | Asn | Leu | Tyr | Val 490 | Ser | Leu | Leu | Leu 495 | Leu | Tyr |
| Lys | Thr | Phe | Gly 500 | Arg | Lys | Leu | His | Leu 505 | Tyr | Ser | His | Pro | Ile 510 | Ile | Leu |
| Gly | Phe | Arg 515 | Lys | Ile | Pro | Met | Gly 520 | Val | Gly | Leu | Ser | Pro 525 | Phe | Leu | Leu |
| Ala | Gln 530 | Phe | Thr | Ser | Ala | Ile 535 | Cys | Ser | Val | Val | Arg 540 | Arg | Ala | Phe | Pro |
| His 545 | Cys | Leu | Ala | Phe | Ser 550 | Tyr | Met | Asp | Asp | Val 555 | Val | Leu | Gly | Ala | Lys 560 |
| Ser | Val | Gln | His 565 | Leu | Glu | Ser | Leu | Phe 570 | Thr | Ala | Val | Thr | Asn 575 | Phe | Leu |
| Leu | Ser | Leu | Gly 580 | Ile | His | Leu | Asn | Pro 585 | Asn | Lys | Thr | Lys | Arg 590 | Trp | Gly |
| Tyr | Ser | Leu 595 | Asn | Phe | Met | Gly | Tyr 600 | Val | Ile | Gly | Ser | Trp 605 | Gly | Thr | Ile |
| Pro | Gln 610 | Glu | His | Ile | Val | Gln 615 | Lys | Ile | Lys | Gln | Cys 620 | Phe | Arg | Lys | Leu |
| Pro 625 | Val | Asn | Arg | Pro | Ile 630 | Asp | Trp | Lys | Val | Cys 635 | Gln | Arg | Ile | Val | Gly 640 |
| Leu | Leu | Gly | Phe | Ala 645 | Ala | Pro | Phe | Thr | Gln 650 | Cys | Gly | Tyr | Pro | Ala 655 | Leu |
| Met | Pro | Leu | Tyr 660 | Ala | Cys | Ile | Gln | Ser 665 | Lys | Gln | Ala | Phe | Thr 670 | Phe | Ser |
| Pro | Thr | Tyr 675 | Lys | Ala | Phe | Leu | Cys 680 | Lys | Gln | Tyr | Leu | Asn 685 | Leu | Tyr | Pro |

| | | | | | | | | | | | | | | |
|---|---|---|---|---|---|---|---|---|---|---|---|---|---|---|
| Val | Ala 690 | Arg | Gln | Arg | Pro | Gly 695 | Leu | Cys | Gln | Val | Phe 700 | Ala | Asp | Ala | Thr |
| Pro 705 | Thr | Gly | Trp | Gly | Leu 710 | Ala | Ile | Gly | His | Gln 715 | Arg | Met | Arg | Gly | Thr 720 |
| Phe | Val | Ala | Pro | Leu 725 | Pro | Ile | His | Thr | Ala 730 | Glu | Leu | Leu | Ala | Ala 735 | Cys |
| Phe | Ala | Arg | Ser 740 | Arg | Ser | Gly | Ala | Lys 745 | Leu | Ile | Gly | Thr | Asp 750 | Asn | Ser |
| Val | Val | Leu 755 | Ser | Arg | Lys | Tyr | Thr 760 | Ser | Phe | Pro | Trp | Leu 765 | Leu | Gly | Cys |
| Ala | Ala 770 | Asn | Trp | Ile | Leu | Arg 775 | Gly | Thr | Ser | Phe | Val 780 | Tyr | Val | Pro | Ser |
| Ala 785 | Leu | Asn | Pro | Ala | Asp 790 | Asp | Pro | Ser | Arg | Gly 795 | Arg | Leu | Gly | Leu | Tyr 800 |
| Arg | Pro | Leu | Leu | Arg 805 | Leu | Pro | Phe | Arg | Pro 810 | Thr | Thr | Gly | Arg | Thr 815 | Ser |
| Leu | Tyr | Ala | Val 820 | Ser | Pro | Ser | Val | Pro 825 | Ser | His | Leu | Pro | Asp 830 | Arg | Val |
| His | Phe | Ala 835 | Ser | Pro | Leu | His | Val 840 | Ala | Trp | Arg | Pro | Pro 845 | | | |